US011198913B2

(12) United States Patent
Reshatoff et al.

(10) Patent No.: US 11,198,913 B2
(45) Date of Patent: Dec. 14, 2021

(54) **COMPOSITIONS, KITS AND RELATED METHODS FOR THE DETECTION AND/OR MONITORING OF *LISTERIA***

(71) Applicant: Gen-Probe Incorporated, San Diego, CA (US)

(72) Inventors: Michael R. Reshatoff, San Diego, CA (US); Kristin W. Livezey, Encinitas, CA (US); James J. Hogan, Coronado, CA (US)

(73) Assignee: GEN-PROBE INCORPORATED, San Diego, CA (US)

(*) Notice: Subject to any disclaimer, the term of this patent is extended or adjusted under 35 U.S.C. 154(b) by 78 days.

(21) Appl. No.: 16/663,642

(22) Filed: Oct. 25, 2019

(65) Prior Publication Data
US 2020/0048684 A1    Feb. 13, 2020

Related U.S. Application Data

(60) Division of application No. 15/424,052, filed on Feb. 3, 2017, now Pat. No. 10,501,812, which is a division of application No. 14/268,107, filed on May 2, 2014, now Pat. No. 9,593,383, which is a continuation of application No. 12/649,249, filed on Dec. 29, 2009, now Pat. No. 8,748,133.

(60) Provisional application No. 61/141,651, filed on Dec. 30, 2008.

(51) Int. Cl.
*C12Q 1/689* (2018.01)
*C12Q 1/6816* (2018.01)
*C12Q 1/6865* (2018.01)

(52) U.S. Cl.
CPC ........... *C12Q 1/689* (2013.01); *C12Q 1/6816* (2013.01); *C12Q 1/6865* (2013.01)

(58) Field of Classification Search
CPC ..... C12Q 1/689; C12Q 1/6816; C12Q 1/6865
See application file for complete search history.

(56) References Cited

U.S. PATENT DOCUMENTS

| | | | |
|---|---|---|---|
| 8,748,133 B2 | 6/2014 | Reshatoff et al. | |
| 9,593,383 B2 | 3/2017 | Reshatoff et al. | |
| 10,501,812 B2 | 12/2019 | Reshatoff et al. | |
| 2005/0142584 A1* | 6/2005 | Willson | C12Q 1/689 435/6.16 |
| 2005/0266468 A1 | 12/2005 | Bedzyk et al. | |
| 2009/0286249 A1 | 11/2009 | Becker et al. | |
| 2010/0173305 A1 | 7/2010 | Reshatoff et al. | |
| 2014/0287411 A1 | 9/2014 | Reshatoff et al. | |
| 2017/0211132 A1 | 7/2017 | Reshatoff et al. | |

FOREIGN PATENT DOCUMENTS

| | | |
|---|---|---|
| EP | 03144294 A2 | 5/1989 |
| EP | 01978111 A1 | 10/2008 |
| WO | WO 1991/001384 A1 | 2/1991 |
| WO | WO 1997/032036 A1 | 9/1997 |
| WO | WO 2005/063283 A1 | 7/2005 |

OTHER PUBLICATIONS

Lowe, et al., "A computer program for selection of oligonucleotide primers for polymerase chain reactions," Nucleic Acids Research, vol. 18, No. 7, pp. 1757-1761, (1990).
Somer, et al., "A PCR Method Based on 16S rRNA sequence for Simultaneous Detection of the Genus *Listeria* and the Species *Listeria monocytogenes* in Food Products," Journal of Food protection, vol. 66, No. 9, pp. 1658-1665, (2003).
Ehresmann, et al., "Recent Progress in the Determination of the Primary Sequence of the 16S RNA of *Escherichia Coli*," FEBS Letters, vol. 84, No. 2, pp. 337-341, (Dec. 1977).
Holland, et al., "PCR Detection of *Escherichia coli* O157:H7 Directly from Stools: Evaluation of Commercial Extraction Methods for Purifying Fecal DNA," Journal of Clinical Microbiology, vol. 38, No. 11, pp. 4108-4113, (Nov. 2000).
Wang, et al., 16S rRNA-based probes and polymerase chain reaction method to detect Listeria monocytogenes cells added to foods, Applied and Environmental Microbiology, 58(9), p. 2827-2831, (1992).
U.S. Appl. No. 15/424,052 Non-Final Office Action dated Aug. 2, 2018.
U.S. Appl. No. 15/424,052 Final Office Action dated Mar. 28, 2019.
U.S. Appl. No. 15/424,052 Notice of Allowance dated Jul. 25, 2019.
U.S. Appl. No. 14/268,107 Restriction Requirement dated Jan. 15, 2016.
U.S. Appl. No. 14/268,107 Non-Final Office Action dated May 3, 2016.
U.S. Appl. No. 14/268,107 Notice of Allowance and Interview Summary dated Nov. 2, 2016.
U.S. Appl. No. 12/649,249 Restriction Requirement dated Aug. 20, 2012.
U.S. Appl. No. 12/649,249 Restriction Requirement dated May 15, 2013.
U.S. Appl. No. 12/649,249 Non-Final Office Action dated Sep. 24, 2012.
U.S. Appl. No. 12/649,249 Final Rejection dated Sep. 10, 2013.
U.S. Appl. No. 12/649,249 Notice of Allowance dated Jan. 27, 2014.
Australian Patent No. 2009335053 Office Action dated Jul. 30, 2012.
Australian Patent No. 2009335053 Notice of Acceptance dated Jul. 19, 2013.
EP 09795674.2 Communication Pursuant to Art. 94(3) EPC dated Oct. 24, 2012.
PCT/US2009/069746 International Search Report and Written Opinion dated Mar. 8, 2010.

(Continued)

*Primary Examiner* — Cynthia B Wilder
(74) *Attorney, Agent, or Firm* — Alston & Bird LLP; Jeffrey E. Landes

(57) ABSTRACT

Provided are compositions, kits, and methods for the identification of *Listeria*. In certain aspects and embodiments, the compositions, kits, and methods may provide improvements in relation to specificity, sensitivity, and speed of detection.

20 Claims, 4 Drawing Sheets

Specification includes a Sequence Listing.

(56) References Cited

OTHER PUBLICATIONS

EP Application No. 09795674.2 Office Action dated Jan. 31, 2014.
EP Application No. 09795674.2 Communication under Rule 71(3) dated Jul. 30, 2014.
JP Application No. 2011-543724 Office Action dated Dec. 25, 2014.
PCT/US2009/069746 International Preliminary Report on Patentability dated Jul. 5, 2011.
U.S. Appl. No. 15/424,052, filed Feb. 3, 2017, U.S. Pat. No. 10,501,812, Issued.
U.S. Appl. No. 14/268,107, filed May 2, 2014, U.S. Pat. No. 9,593,383, Issued.
U.S. Appl. No. 12/549,249, filed Dec. 29, 2009, U.S. Pat. No. 8,748,133, Issued.
U.S. Appl. No. 61/141,651, filed Dec. 30, 2008, Expired.

\* cited by examiner

FIG. 2

| | | |
|---|---|---|
| E.coli_J01859 | 350 5' | GCAGCAGTGGGGAATATTGCACAATGGGCGCAAGCCTGATGCAGCCATGCCGCGTGT |
| L.monocytogenes_M58822.ATCC35152 | 360 5' | GCAGCAGTAGGGAATCTTCCGCAATGACGAAGTCTGACGAGCAACGCCGCGTGT |
| L.innocua_X98527.ATCC33090 | 296 5' | GCAGCAGTAGGGAATCTTCCGCAATGACGAAGTCTGACGAGCAACGCCGCGTGT |
| L.ivanovii_GP894_ATCCF4081 | 332 5' | GCAGCAGTAGGGAATCTTCCGCAATGACGAAAGTCTGACGAGCAACGCCGCGTGT |
| L.seeligeri_GP895_ATCCF4088 | 271 5' | GCAGCAGTAGGGAATCTTCCGCAATGACGAAAGTCTGACGAGCAACGCCGCGTGT |
| L.welshimeri_GP896_ATCCF4082 | 326 5' | GCAGCAGTAGGGAATCTTCCGCAATGACGAAAGTCTGACGAGCAACGCCGCGTGT |
| L.murrayi_GP898_ATCCF4076 | 337 5' | GCAGCAGTAGGGAATCTTCCGCAATGACGAAAGTCTGACGAGCAACGCCGCGTGT |
| L.grayi_X98526.ATCC19120 | 318 5' | GCAGCAATAGGGAAACTTCCGCAATGACGAAAGTCTGACGAGCAACGCCGCGTGT |
| B.thermosphacta_GP829_ATCC11509 | 310 5' | GCAGCAGTAGGGAATCTTCGGCAATGACGAAAGTCTGACCGAGCAACGCCGCGTGA |
| E.rhusiopathiae_GP595_ATCC19414 | 290 5' | GCAGCAGTAGGGAATTTCGGCAATGGGGAAACCCTGACCGAGCAACGCCGCGTGA |

| | | |
|---|---|---|
| E.coli_J01859 | 407 5' | ATGAAGAAGGC-CTTCGGGTTGTAAAGTACTTTCAGCGGGGAGGAAGGGAGTAAAGT |
| L.monocytogenes_M58822.ATCC35152 | 417 5' | ATGAAGAAGGT-TTTCGGATCGTAAAGTACTGTGTTAGAGAAGAACAAGGATAAGA |
| L.innocua_X98527.ATCC33090 | 353 5' | ATGAAGAAGGT-TTTCGGATCGTAAAGTACTGTGTTAGAGAAGAACAAGGATAAGA |
| L.ivanovii_GP894_ATCCF4081 | 389 5' | ATGAAGAAGGT-TTTCGGATCGTAAAGTACTGTGTTAGAGAAGAACAAGGATAAGA |
| L.seeligeri_GP895_ATCCF4088 | 328 5' | ATGAAGAAGGT-TTTCGGATCGTAAAGTACTGTGTTAGAGAAGAACAAGGATAAGA |
| L.welshimeri_GP896_ATCCF4082 | 383 5' | ATGAAGAAGGT-TTTCGGATCGTAAAGTACTGTGTTAGAGAAGAACAAGGATAAGA |
| L.murrayi_GP898_ATCCF4076 | 394 5' | GTGAAGAAGGT-TTTCGGATCGTAAAGCACTGTGTTGTTAGAGAAGAACAAGGATAAGA |
| L.grayi_X98526.ATCC19120 | 375 5' | GTGAAGAAGGT-TTTCGGATCGTAAAGCACTGTGTTGTTAGAGAAGAACAAGGATAAGA |
| B.thermosphacta_GP829_ATCC11509 | 367 5' | GCGAAGAAGGCC-TTCGGGTCGTAAAGCTCTGTTGTTAGAGAAGAACATGGTGAGA |
| E.rhusiopathiae_GP595_ATCC19414 | 347 5' | GTGAAGACGGCC-TTCGGGTTGTAAAGCTCTGTTGTTGTAAGGGAAGAACGATAGGAAGA |

| | | | |
|---|---|---|---|
| E.coli_J01859 | 463 5' | TAATACCTTTGCTCATTGACGTTACCCGCAGAAGAAGCACCGG | (SEQ ID NO:103) |
| L.monocytogenes_M58822.ATCC35152 | 473 5' | GTAACTGCTTGTCCCTTGACGGTATCTAACCAGAAAGCCACGG | (SEQ ID NO:104) |
| L.innocua_X98527.ATCC33090 | 409 5' | GTAACTGCTTGTCCCTTGACGGTATCTAACCAGAAAGCCACGG | (SEQ ID NO:105) |
| L.ivanovii_GP894_ATCCF4081 | 445 5' | GTAACTGCTTGTCCCTTGACGGTATCTAACCAGAAAGCCACGG | (SEQ ID NO:106) |
| L.seeligeri_GP895_ATCCF4088 | 384 5' | GTAACTGCTTGTCCCTTGACGGTATCTAACCAGAAAGCCACGG | (SEQ ID NO:107) |
| L.welshimeri_GP896_ATCCF4082 | 439 5' | GTAACTGCTTGTCCCTTGACGGTATCTAACCAGAAAGCCACGG | (SEQ ID NO:108) |
| L.murrayi_GP898_ATCCF4076 | 450 5' | GTAACTGCTTGTCCCTTGACGGTATCTAACCAGAAAGCCACGG | (SEQ ID NO:109) |
| L.grayi_X98526.ATCC19120 | 431 5' | GTAACTGCTTGTCCCTTGACGGTATCTAACTAACCAGAAAGCCACGG | (SEQ ID NO:110) |
| B.thermosphacta_GP829_ATCC11509 | 423 5' | GTAACTGTTCACCCCTTGACGGTATCTAACCAGAAAGCCACGG | (SEQ ID NO:111) |
| E.rhusiopathiae_GP595_ATCC19414 | 403 5' | GGGAATGCTTCTTATATGACGTACCTTACCAGAAAGCCACGG | (SEQ ID NO:112) |

FIG. 3

| Organism | Pos | | Sequence |
|---|---|---|---|
| E.coli_J01859 | 1180 | 5' | GGTGGGGATGACGTCAAGTCATCATGGCCCTTACGACCAGGGCTACACACGTGCTAC |
| L.monocytogenes_M58822.ATCC35152 | 1189 | 5' | GGTGGGGATGACGTCAAATCATCATGCCCCCCTTATGACCTGGGCTACACACGTGCTAC |
| L.innocua_X98527.ATCC33090 | 1125 | 5' | GGTGGGGATGACGTCAAATCATCATGCCCCTTATGACCTGGGCTACACACGTGCTAC |
| L.ivanovii_GP894_ATCCF4081 | 1161 | 5' | GGTGGGGATGACGTCAAATCATCATGCCCCTTATGACCTGGGCTACACACGTGCTAC |
| L.seeligeri_GP895_ATCCF4088 | 1100 | 5' | GGTGGGGATGACGTCAAATCATCATGCCCCTTATGACCTGGGCTACACACGTGCTAC |
| L.welshimeri_GP896_ATCCF4082 | 1155 | 5' | GGTGGGGATGACGTCAAATCATCATGCCCCTTATGACCTGGGCTACACACGTGCTAC |
| L.murrayi_GP898_ATCCF4076 | 1167 | 5' | GGTGGGGATGACGTCAAATCATCATGCCCCTTATGACCTGGGCTACACACGTGCTAC |
| L.grayi_X98526.ATCC19120 | 1148 | 5' | GGTGGGGATGACGTCAAATCATCATGCCCCTTATGACCTGGGCTACACACGTGCTAC |
| B.thermosphacta_GP829_ATCC11509 | 1139 | 5' | GGTGGGGATGACGTCAAATCATCATGCCCCTTATGACCTGGGCTACACACGTGCTAC |
| E.rhusiopathiae_GP595_ATCC19414 | 1106 | 5' | GGTGGGGATGACGTCAAATCATCATGCCCCTTATGATCTGGGCTACACACGTACTAC |
| | | | |
| E.coli_J01859 | 1237 | 5' | AATGGCGCATACAAAGAGAAGCGACCTCGCGAGAGCAAGCGGACCTCATAAAGTGCG |
| L.monocytogenes_M58822.ATCC35152 | 1246 | 5' | AATGGATAGTACAAAGGGTNGCGAAGCCGGAGCTGGAGCTAATCCCATAAAACTAT |
| L.innocua_X98527.ATCC33090 | 1182 | 5' | AATGGATGTACAAAGGGTCGCGAAGCCGGAGCTGGAGCTAATCCCATAAAACCAT |
| L.ivanovii_GP894_ATCCF4081 | 1218 | 5' | AATGGATGTACAAAGGGTCGCGAAGCCGGAGCTGGAGCTAATCCCATAAAACCAT |
| L.seeligeri_GP895_ATCCF4088 | 1157 | 5' | AATGGATGTACAAAGGGTAGCGAAGCCGGAGCTGGAGCTAATCCCATAAAACCAT |
| L.welshimeri_GP896_ATCCF4082 | 1212 | 5' | AATGGATGTACAAAGGGTCGCGAAGCCGGAGCTGGAGCTAATCCCATAAAACCAT |
| L.murrayi_GP898_ATCCF4076 | 1224 | 5' | AATGGATGATACAAAGGGTCGCGAAGCCGGAGCTGGAGCTAAGCTAATCCCATAAAATCAT |
| L.grayi_X98526.ATCC19120 | 1205 | 5' | AATGGATGATACAAAGGGTCGCGAA-CCGCGAAGCCGGAGCTGGAGCTAATCCCATAAAATTAT |
| B.thermosphacta_GP829_ATCC11509 | 1196 | 5' | AATGGATAATACAAAGGGTCGCGAAGCCGGAGCAGCAGCGGAGCGATGCGGAGCGATGCGAAGTACG |
| E.rhusiopathiae_GP595_ATCC19414 | 1163 | 5' | AATGGCGTATACAGAGAGGGCAGCAGCAGCGAAGCAGCAGCGATGCGGAGCGAATCTCAGAAAGTACG |
| | | | |
| E.coli_J01859 | 1294 | 5' | TCGTAGTCCGGATTGGAGTCTGCAACTCGACTCCATGAAGTCGGAATCGCTAGTAAT |
| L.monocytogenes_M58822.ATCC35152 | 1303 | 5' | TCTCAGTTCGGATTGTAGGCTGCAACTCGCCTACATGAAGCCGGAATCGCTAGTAAT |
| L.innocua_X98527.ATCC33090 | 1239 | 5' | TCTCAGTTCGGATTGTAGGCTGCAACTCGCCTACATGAAGCCGGAATCGCTAGTAAT |
| L.ivanovii_GP894_ATCCF4081 | 1275 | 5' | TCTCAGTTCGGATTGTAGGCTGCAACTCGCCTACATGAAGCCGGAATCGCTAGTAAT |
| L.seeligeri_GP895_ATCCF4088 | 1214 | 5' | TCTCAGTTCGGATTGTAGGCTGCAACTCGCCTACATGAAGCCGGAATCGCTAGTAAT |
| L.welshimeri_GP896_ATCCF4082 | 1269 | 5' | TCTCAGTTCGGATTGTAGGCTGCAACTCGCCTACATGAAGCCGGAATCGCTAGTAAT |
| L.murrayi_GP898_ATCCF4076 | 1281 | 5' | TCTCAGTTCGGATTGTAGGCTGCAACTCGCCTACATGAAGCCGGAATCGCTAGTAAT |
| L.grayi_X98526.ATCC19120 | 1261 | 5' | TCTCAGTTCGGATTGTAGGCTGCAACTCGCCTGCATGAAGCCGGAATCGCTAGTAAT |
| B.thermosphacta_GP829_ATCC11509 | 1253 | 5' | TCTCAGTTCGGATTGCAGGCTGCAACTCGCCTGCATGAAGCCGGAATCGCTAGTAAT |
| E.rhusiopathiae_GP595_ATCC19414 | 1220 | 5' | TCTCAGTTCGGATTGGAGTCTGCAACTCGACTCCATGAAGTCGGAATCGCTAGTAAT |

FIG. 3 (Continued)

| | | | | |
|---|---|---|---|---|
| E.coli_J01859 | 1351 | 5' | CGTGGATCAGAATGCCACGG | (SEQ ID NO:113) |
| L.monocytogenes_M58822.ATCC35152 | 1360 | 5' | CGTGGATCAGCATGCCACGG | (SEQ ID NO:114) |
| L.innocua_X98527.ATCC33090 | 1296 | 5' | CGTGGATCAGCATGCCACGG | (SEQ ID NO:115) |
| L.ivanovii_GP894_ATCCF4081 | 1332 | 5' | CGCGGATCAGCATGCCGCGG | (SEQ ID NO:116) |
| L.seeligeri_GP895_ATCCF4088 | 1271 | 5' | CGTGGATCAGCATGCCACGG | (SEQ ID NO:117) |
| L.welshimeri_GP896_ATCCF4082 | 1326 | 5' | CGTGGATCAGCATGCCACGG | (SEQ ID NO:118) |
| L.murrayi_GP898_ATCCF4076 | 1338 | 5' | CGCGGATCAGCATGCCGCGG | (SEQ ID NO:119) |
| L.grayi_X98526.ATCC19120 | 1318 | 5' | CGCGGATCAGCATGCCGCGG | (SEQ ID NO:120) |
| B.thermosphacta_GP829_ATCC11509 | 1310 | 5' | CGTAGATCAGCATGCTACGG | (SEQ ID NO:121) |
| E.rhusiopathiae_GP595_ATCC19414 | 1277 | 5' | CGCGGATCAGAATGCCGCGG | (SEQ ID NO:122) | ical amplification reactions which provide improvements in relation to specificity, sensitivity, or speed of detection as well as other advantages.

COMPOSITIONS, KITS AND RELATED METHODS FOR THE DETECTION AND/OR MONITORING OF *LISTERIA*

CROSS-REFERENCE TO RELATED APPLICATIONS

This application is a divisional of U.S. application Ser. No. 15/424,052, filed Feb. 3, 2017, which is a divisional of U.S. application Ser. No. 14/268,107, filed May 2, 2014, issued as U.S. Pat. No. 9,593,383, which is a continuation of U.S. application Ser. No. 12/649,249 filed Dec. 29, 2009, issued as U.S. Pat. No. 8,748,133, which claims the benefit of U.S. Provisional Application No. 61/141,651 filed Dec. 30, 2008, each of which is hereby incorporated by reference in their entireties for all purposes.

SEQUENCE LISTING

The Sequence Listing written in file 538673SeqListing.txt is 36 kilobytes in size, was created Oct. 22, 2019, and is hereby incorporated by reference

FIELD

The inventions disclosed herein relate to microorganisms and to compositions and mechanisms for the detection thereof.

BACKGROUND

This application relates to compositions and methods for detecting *Listeria*. In certain aspects and embodiments, particular regions of the *Listeria* 16S rRNA have been identified as preferred targets for nucleic acid amplification reactions.

*Listeria* is a gram-positive bacteria found in soil and water. Vegetables can become contaminated from the soil or from manure used as fertilizer. Animals can carry the bacterium without appearing ill and can contaminate foods of animal origin such as meats and dairy products. Listeriosis, a serious infection caused by eating food contaminated with the bacterium *Listeria monocytogenes*, has recently been recognized as an important public health problem in the United States. In the United States, an estimated 2,500 persons become seriously ill with listeriosis each year. Of these, 500 die. At increased risk are pregnant women, newborns, persons with weakened immune systems; persons with cancer, diabetes, or kidney disease; persons with AIDS, persons who take glucocorticosteroid medications, and the elderly. Species include *L. monocytogenes, L. innocua, L. welshimeri, L. ivanovii, L. seeligeri, L. grayi*, and *L. murrayi*.

SUMMARY

The present invention relates to compositions, kits, and methods used in the detection of *Listeria*. The invention is based in part on the discovery that certain *Listeria* sequences are surprisingly efficacious for the detection of *Listeria*. In certain aspects and embodiments, particular regions of the *Listeria* 16S rRNA have been identified as preferred targets for nucleic acid amplification reactions which provide improvements in relation to specificity, sensitivity, or speed of detection as well as other advantages.

In some preferred aspects, there are provided compositions for use in a *Listeria* transcription-mediated amplification assay (hereinafter "TMA"). In some preferred aspects, there are provided kits for performing a *Listeria* transcription-mediated amplification assay. In some preferred aspects, there are provided methods for performing a *Listeria* transcription-mediated amplification assay. In certain preferred embodiments, the compositions, kits, and/or methods may include or use one or more oligonucleotides such as a: T7 provider oligonucleotide, primer oligonucleotide, detection oligonucleotide, blocker oligonucleotide, Torch oligonucleotide, and the like.

Therefore, according to one aspect, there are provided compositions for use in a *Listeria* nucleic acid amplification assay. In certain preferred embodiments, the compositions include a T7 provider oligonucleotide and a primer oligonucleotide; in which the T7 provider oligonucleotide targets a sequence in a region of *Listeria* nucleic acid corresponding to nucleotide positions of about 364-440 of *E. coli* 16S rRNA and the primer oligonucleotide targets a sequence in a region of *Listeria* nucleic acid, in which the T7 provider oligonucleotide and primer oligonucleotide used in the amplification assay target opposite strands of the *Listeria* nucleic acid sequence to be amplified.

In a second aspect, there are provided compositions for use in a *Listeria* nucleic acid amplification assay. In certain preferred embodiments, the compositions include a first T7 provider oligonucleotide having the sequence of SEQ ID NO: 13 or complement and a second T7 provider oligonucleotide having the sequence of SEQ ID NO: 14 or complement. In another preferred embodiment, the primer oligonucleotide has the sequence of SEQ ID NO: 23 or complement.

In a third aspect, there are provided compositions for use in a *Listeria* nucleic acid amplification assay. In certain preferred embodiments, the compositions include two or more T7 provider oligonucleotides and one or more primer oligonucleotides. In certain preferred embodiments, the two or more T7 provider oligonucleotides and the one or more primer oligonucleotides are configured and arranged such that *L. monocytogenes, L. innocua, L. grayi, L. ivanovii, L. welshimeri, L. murrayi*, and *L. seeligeri*, are amplified under the *Listeria* nucleic acid amplification assay conditions. In certain preferred embodiments, the two or more T7 provider oligonucleotides and the one or more primer oligonucleotides are configured and arranged such that *Brochothrix thermosphacta* and *Erysipelothrix rhusiopathiae* are not substantially amplified under the *Listeria* nucleic acid amplification assay conditions.

In a fourth aspect, there are provided kits that include the compositions provided herein. In certain preferred embodiments of the aspects provided herein, the kits include a T7 provider oligonucleotide and a primer oligonucleotide, in which the T7 provider oligonucleotide targets a sequence in a region of *Listeria* nucleic acid corresponding to nucleotide positions of about 364-440 of *E. coli* 16S rRNA and the primer oligonucleotide targets a sequence in a region of *Listeria* nucleic acid, in which the T7 provider oligonucleotide and primer oligonucleotide used in the amplification assay target opposite strands of the *Listeria* nucleic acid sequence to be amplified.

In a fifth aspect, there are provided kits that include the compositions provided herein. In certain preferred embodiments of the aspects provided herein, the kits include a first T7 provider oligonucleotide having the sequence of SEQ ID NO: 13 or complement and a second T7 provider oligonucleotide having the sequence of SEQ ID NO: 14 or complement. In another preferred embodiment, the primer oligonucleotide has the sequence of SEQ ID NO: 23 or complement.

In a sixth aspect, there are provided kits that include the compositions provided herein. In certain preferred embodiments of the aspects provided herein, the kits include two or more T7 provider oligonucleotides and one or more primer oligonucleotides. In certain preferred embodiments, the two or more T7 provider oligonucleotides and the one or more primer oligonucleotides are configured and arranged such that *L. monocytogenes, L. innocua, L. grayi, L. ivanovii, L. welshimeri, L. murrayi*, and *L. seeligeri*, are amplified under the *Listeria* nucleic acid amplification assay conditions. In certain preferred embodiments, the two or more T7 provider oligonucleotides and the one or more primer oligonucleotides are configured and arranged such that *Brochothrix thermosphacta* and *Erysipelothrix rhusiopathiae* are not substantially amplified under the *Listeria* nucleic acid amplification assay conditions.

In a seventh aspect, there are provided methods for detecting the presence of *Listeria* in a sample using the compositions and/or kits provided herein. In certain preferred embodiments of the aspects provided herein, the methods use a T7 provider oligonucleotide and a primer oligonucleotide, in which the T7 provider oligonucleotide targets a sequence in a region of *Listeria* nucleic acid corresponding to nucleotide positions of about 364-440 of *E. coli* 16S rRNA and the primer oligonucleotide targets a sequence in a region of *Listeria* nucleic acid, in which the T7 provider oligonucleotide and primer oligonucleotide used in the amplification assay target opposite strands of the *Listeria* nucleic acid sequence to be amplified.

In an eighth aspect, there are provided methods for detecting the presence of *Listeria* in a sample using the compositions and/or kits provided herein. In certain preferred embodiments of the aspects provided herein, the methods use a first T7 provider oligonucleotide having the sequence of SEQ ID NO: 13 or complement and a second T7 provider oligonucleotide having the sequence of SEQ ID NO: 14 or complement. In another preferred embodiment, the primer oligonucleotide has the sequence of SEQ ID NO: 23 or complement.

In a ninth aspect, there are provided methods for detecting the presence of *Listeria* in a sample using the compositions and/or kits provided herein. In certain preferred embodiments of the aspects provided herein, the methods use two or more T7 provider oligonucleotides and one or more primer oligonucleotides. In certain preferred embodiments, the two or more T7 provider oligonucleotides and the one or more primer oligonucleotides are configured and arranged such that *L. monocytogenes, L. innocua, L. grayi, L. ivanovii, L. welshimeri, L. murrayi*, and *L. seeligeri*, are amplified under the *Listeria* nucleic acid amplification assay conditions. In certain preferred embodiments, the two or more T7 provider oligonucleotides and the one or more primer oligonucleotides are configured and arranged such that *Brochothrix thermosphacta* and *Erysipelothrix rhusiopathiae* are not substantially amplified under the *Listeria* nucleic acid amplification assay conditions.

In one particularly preferred embodiment of the aspects provided herein, the T7 provider oligonucleotide has an adenine at the nucleotide position that is complementary to the nucleotide position in a *Listeria* nucleic acid sequence corresponding to nucleotide position 407 of *E. coli* 16S rRNA. In another particularly preferred embodiment of the aspects provided herein, the T7 provider oligonucleotide has a guanine at the nucleotide position that is complementary to the nucleotide position in a *Listeria* nucleic acid sequence corresponding to nucleotide position 407 of *E. coli* 16S rRNA. In one preferred embodiment, the T7 provider oligonucleotide has a sequence selected from the sequences of SEQ ID NOs: 8, 9, 10, 11, 12, 13, 14, 15, or complements. In a particularly preferred embodiment of the aspects provided herein, the T7 provider oligonucleotide targets a sequence in a region of *Listeria* nucleic acid corresponding to nucleotide positions of about 398-417 of *E. coli* 16S rRNA. In one particularly preferred embodiment of the aspects provided herein, the T7 provider oligonucleotides comprises the sequence of SEQ ID NO: 13 or complement. In another particularly preferred embodiment of the aspects provided herein, the T7 provider oligonucleotides comprises the sequence of SEQ ID NO: 14 or complement.

In another particularly preferred embodiment of the aspects provided herein, the composition further comprises a second T7 provider. In one particularly preferred embodiment of the aspects provided herein, the composition includes a first T7 provider oligonucleotide having an adenine at the nucleotide position that is complementary to the nucleotide position in a *Listeria* nucleic acid sequence corresponding to nucleotide position 407 of *E. coli* 16S rRNA, and a second T7 provider oligonucleotide having a guanine at the nucleotide position that is complementary to the nucleotide position in a *Listeria* nucleic acid sequence corresponding to nucleotide position 407 of *E. coli* 16S rRNA. In another preferred embodiment, at least one of the T7 provider oligonucleotides has a sequence selected from the sequences of SEQ ID NOs: 8, 9, 10, 11, 12, 13, 14, 15, or complements. In one preferred embodiment of the aspects provided herein, at least one of the T7 provider oligonucleotides targets a sequence in a region of *Listeria* nucleic acid corresponding to nucleotide positions of about 398-417 of *E. coli* 16S rRNA. In another particularly preferred embodiment of the aspects provided herein in which the composition includes a first and a second T7 provider oligonucleotide, the first and the second T7 provider oligonucleotide each target a sequence in a region of *Listeria* nucleic acid corresponding to nucleotide positions of about 398-417 of *E. coli* 16S rRNA. In other particularly preferred embodiments of the aspects provided herein in which the composition includes a first and a second T7 provider oligonucleotide, the first T7 provider oligonucleotides comprises the sequence of SEQ ID NO: 13 or complement, and the second T7 provider oligonucleotides comprises the sequence of SEQ ID NO: 14 or complement.

In one preferred embodiment of the aspects provided herein, the primer oligonucleotide targets a sequence in a region of *Listeria* nucleic acid corresponding to nucleotide positions of about 439-505 of *E. coli* 16S rRNA. In a preferred embodiment, the primer oligonucleotide targets a sequence in a region of *Listeria* nucleic acid corresponding to nucleotide positions of about 480-501 of *E. coli* 16S rRNA. In yet another preferred embodiment, the primer oligonucleotide has a sequence selected from the sequences of SEQ ID NOs: 16, 17, 18, 19, 20, 21, 22, 23, or complements. In a particularly preferred embodiment, the primer oligonucleotide comprises the sequence of SEQ ID NO: 23 or complement.

In certain preferred embodiments of the aspects provided herein, the T7 provider oligonucleotide includes 15-35 nucleotides that are at least 70%; or 75%; or 80%; or 85%; or 90%; or 100% complementary to the targeted *Listeria* nucleic acid sequence. In certain preferred embodiments, the T7 provider oligonucleotide includes 15-35 nucleotides that are complementary to the targeted *Listeria* nucleic acid sequence but have 1 mismatch; or 2 mismatches; or 3 mismatches; or 4 mismatches, or 5 mismatches as compared to the targeted nucleic acid sequence within the 15-35 complementary nucleotides.

In some preferred embodiments of the aspects provided herein, one or more additional oligonucleotide types and/or other amplification reagents that serve to facilitate or improve one or more aspects of the transcription-mediated amplification reaction may be included. For example, in a preferred embodiment, in addition to a T7 provider oligonucleotide and/or a primer oligonucleotide, additional oligonucleotides may further include one or more of a: detection oligonucleotide, blocker oligonucleotide, target capture oligonucleotide, helper oligonucleotide, and the like.

In some preferred embodiments of the aspects provided herein, the compositions, kits, and/or methods may further include or use a detection oligonucleotide, preferably a torch oligonucleotide or an acridinium ester probe. In one preferred embodiment, the detection oligonucleotide is a torch oligonucleotide selected from the sequences of SEQ ID NOs: 24-28 or complements. In a particularly preferred embodiment, the detection oligonucleotide is a torch oligonucleotide having the sequence of SEQ ID NO: 27 or complement.

In some preferred embodiments of the aspects provided herein, the compositions, kits, and/or methods may further include or use a blocker oligonucleotide. In one preferred embodiment, the blocker oligonucleotide is selected from the sequences of SEQ ID NOs: 1-7 or complements. In a particularly preferred embodiment, the blocker oligonucleotide has the sequence of SEQ ID NO: 6 or complement.

In some preferred embodiments of the aspects provided herein, the compositions, kits, and/or methods may further include or use a target capture oligonucleotide. In one preferred embodiment, the target capture oligonucleotide is selected from the sequences of SEQ ID NOs: 29-36 or complements. In a particularly preferred embodiment, the target capture oligonucleotide has the sequence of SEQ ID NOs: 31 or complement.

In some preferred embodiments of the aspects provided herein, the compositions, kits, and/or methods may further include or use a helper oligonucleotide.

The terms and concepts of the invention have meanings as set forth herein unless expressly stated to the contrary and/or unless context specifically dictates otherwise. Unless defined otherwise, scientific and technical terms used herein have the same meaning as commonly understood by those skilled in the relevant art. General definitions may be found in technical books relevant to the art of molecular biology, e.g., Dictionary of Microbiology and Molecular Biology, 2nd ed. (Singleton et al., 1994, John Wiley & Sons, New York, N.Y.) or The Harper Collins Dictionary of Biology (Hale & Marham, 1991, Harper Perennial, New York, N.Y.). Unless mentioned otherwise, techniques employed or contemplated herein are standard methodologies well known to one of ordinary skill in the art. The examples included herein illustrate some preferred embodiments. Each reference cited herein is specifically incorporated herein by reference in its entirety.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

The term "nucleic acid" as used herein encompasses a singular "nucleic acid" as well as plural "nucleic acids," and refers to any chain of two or more nucleotides, nucleosides, or nucleobases (e.g., deoxyribonucleotides or ribonucleotides) covalently bonded together. Nucleic acids include, but are not limited to, virus genomes, or portions thereof, either DNA or RNA, bacterial genomes, or portions thereof, fungal, plant or animal genomes, or portions thereof, messenger RNA (mRNA), ribosomal RNA (rRNA), transfer RNA (tRNA), plasmid DNA, mitochondrial DNA, or synthetic DNA or RNA. A nucleic acid may be provided in a linear (e.g., mRNA), circular (e.g., plasmid), or branched form, as well as a double-stranded or single-stranded form. Nucleic acids may include modified bases to alter the function or behavior of the nucleic acid, e.g., addition of a 3'-terminal dideoxynucleotide to block additional nucleotides from being added to the nucleic acid. As used herein, a "sequence" of a nucleic acid refers to the sequence of bases which make up a nucleic acid.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me). As used herein, methoxy oligonucleotides containing "T" residues have a methoxy group at the 2' position of the ribose moiety, and a uracil at the base position of the nucleotide.

A "non-nucleotide unit" as used herein is a unit which does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a "target sequence" to be amplified. Target nucleic acids may be DNA or RNA as described herein, and may be either single-stranded or double-stranded. The target nucleic acid may include other sequences besides the target sequence which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA.

By "isolated" it is meant that a sample containing a target nucleic acid is taken from its natural milieu, but the term does not connote any degree of purification.

The term "target sequence" as used herein refers to the particular nucleotide sequence of the target nucleic acid which is to be amplified. The "target sequence" includes the complexing sequences to which oligonucleotides (e.g., priming oligonucleotides and/or promoter oligonucleotides) complex during the processes of TMA. Where the target nucleic acid is originally single-stranded, the term "target sequence" will also refer to the sequence complementary to the "target sequence" as present in the target nucleic acid. Where the "target nucleic acid" is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

The term "targets a sequence" as used herein in reference to a region of *Listeria* nucleic acid refers to a process whereby an oligonucleotide hybridizes to the target sequence in a manner that allows for amplification and detection as described herein. In one preferred embodiment, the oligonucleotide is complementary with the targeted *Listeria* nucleic acid sequence and contains no mismatches. In another preferred embodiment, the oligonucleotide is complementary but contains 1; or 2; or 3; or 4; or 5 mismatches with the targeted *Listeria* nucleic acid sequence. Preferably, the oligonucleotide that hybridizes to the *Listeria* nucleic acid sequence includes at least 10 to 50; or 12 to 45; or 14 to 40; or 15-35 nucleotides complementary to the target sequence.

The term "fragment" or "region" as used herein in reference to the *Listeria* targeted nucleic acid sequence refers to a piece of contiguous nucleic acid. In certain embodiments, the fragment includes 25; or 50; or 75; or 100; or 125; or 150; or 175; or 200; or 225; or 250; or 300; or 350; or 400; or 450; or 500; or 750; or 1000; or 2000; or 3000 nucleotides.

As used herein, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods disclosed herein, as well as subsequent detection methods. The oligonucleotide may be DNA and/or RNA and/or analogs thereof. The term oligonucleotide does not denote any particular function to the reagent, rather, it is used generically to cover all such reagents described herein. An oligonucleotide may serve various different functions, e.g., it may function as a primer if it is specific for and capable of hybridizing to a complementary strand and can further be extended in the presence of a nucleic acid polymerase, it may provide a promoter if it contains a sequence recognized by an RNA polymerase and allows for transcription (e.g., a T7 Provider), and it may function to prevent hybridization or impede primer extension if appropriately situated and/or modified.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

As used herein, an oligonucleotide "substantially corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from the referred to sequence and still hybridize to the same target nucleic acid sequence. This variation from the nucleic acid may be stated in terms of a percentage of identical bases within the sequence or the percentage of perfectly complementary bases between the probe or primer and its target sequence. Thus, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage can be from 100% to about 90%; in other preferred embodiments, this percentage is from 100% to about 95%. One skilled in the art will understand the various modifications to the hybridization conditions that might be required at various percentages of complementarity to allow hybridization to a specific target sequence without causing an unacceptable level of non-specific hybridization.

A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557, the contents of which are incorporated by reference herein. Helpers may also be used to assist with the hybridization to target nucleic acid sequences and function of primer, target capture and other oligonucleotides.

As used herein, a "blocking moiety" is a substance used to "block" the 3'-terminus of an oligonucleotide or other nucleic acid so that it cannot be efficiently extended by a nucleic acid polymerase.

As used herein, a "priming oligonucleotide" or "primer" is an oligonucleotide, at least the 3'-end of which is complementary to a nucleic acid template, and which complexes (by hydrogen bonding or hybridization) with the template to give a primer: template complex suitable for initiation of synthesis by an RNA- or DNA-dependent DNA polymerase.

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter-provider" or "provider" refers to an oligonucleotide comprising first and second regions, and which is modified to prevent the initiation of DNA synthesis from its 3'-terminus. The "first region" of a promoter-provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 15, 20, 25, 30, 35, 40, 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 provider" is a blocked promoter-provider oligonucleotide that provides an oligonucleotide sequence that is recognized by T7 RNA polymerase.

As used herein, a "terminating oligonucleotide" or "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

An "extender oligonucleotide" or "extend oligo" as used herein refers to an oligonucleotide that is the same sense as the T7 Provider and may act as a helper oligonucleotide that opens up structure or improves specificity.

As used herein, a "detection oligonucleotide" refers to a nucleic acid oligonucleotide that hybridizes specifically to a target sequence, including an amplified sequence, under conditions that promote nucleic acid hybridization, for detection of the target nucleic acid. By "probe oligonucleotide" or "detection probe" is meant a molecule comprising an oligonucleotide having a base sequence partly or completely complementary to a region of a target sequence sought to be detected, so as to hybridize thereto under stringent hybridization conditions.

By "stable" or "stable for detection" is meant that the temperature of a reaction mixture is at least 2° C. below the melting temperature of a nucleic acid duplex.

By "amplification" or "nucleic acid amplification" is meant production of multiple copies of a target nucleic acid that contains at least a portion of the intended specific target nucleic acid sequence, as further described herein. The multiple copies may be referred to as amplicons or amplification products.

The term "amplicon" as used herein refers to the nucleic acid molecule generated during an amplification procedure that is complementary or homologous to a sequence contained within the target sequence.

By "preferentially hybridize" is meant that under stringent hybridization assay conditions, probes hybridize to their target sequences, or replicates thereof, to form stable probe:target hybrids, while at the same time formation of stable probe: non-target hybrids is minimized Thus, a probe hybridizes to a target sequence or replicate thereof to a sufficiently greater extent than to a non-target sequence, to enable one having ordinary skill in the art to accurately quantitate the RNA replicates or complementary DNA (cDNA) of the target sequence formed during the amplification.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm and conditions for nucleic acid hybridization are known in the art.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "perfectly" complementary.

By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

As used herein, a "target capture oligonucleotide" refers to a nucleic acid oligomer that specifically hybridizes to a target sequence in a target nucleic acid by standard base pairing and joins to a binding partner on an immobilized probe to capture the target nucleic acid to a support. One example of a target capture oligomer includes two binding regions: a sequence-binding region (i.e., target-specific portion) and an immobilized probe-binding region, usually on the same oligomer, although the two regions may be present on two different oligomers joined together by one or more linkers.

As used herein, an "immobilized oligonucleotide", "immobilized probe" or "immobilized nucleic acid" refers to a nucleic acid binding partner that joins a target capture oligomer to a support, directly or indirectly. An immobilized oligonucleotide joined to a support facilitates separation of a target capture bound target from unbound material in a sample.

As used herein, a "label" refers to a moiety or compound joined directly or indirectly to a probe that is detected or leads to a detectable signal.

As used herein, structures referred to as "molecular torches" are designed to include distinct regions of self-complementarity (coined "the target binding domain" and "the target closing domain") which are connected by a joining region and which hybridize to one another under predetermined hybridization assay conditions.

As used herein, a "DNA-dependent DNA polymerase" is an enzyme that synthesizes a complementary DNA copy from a DNA template. Examples are DNA polymerase I from E. coli, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially-double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from E. coli and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes other than RNAse H which possess the same or similar activity may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes which selectively degrade RNA target sequences or RNA products of the present invention will be readily apparent to those of ordinary skill in the art.

The term "specificity," in the context of an amplification system, is used herein to refer to the characteristic of an amplification system which describes its ability to distinguish between target and non-target sequences dependent on sequence and assay conditions. In terms of a nucleic acid amplification, specificity generally refers to the ratio of the number of specific amplicons produced to the number of side-products (i.e., the signal-to-noise ratio).

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, i.e., the ratio of specific amplicons to side-products.

As used herein, a "colony forming unit" ("CFU") is used as a measure of viable microorganisms in a sample. A CFU is an individual viable cell capable of forming on a solid medium a visible colony whose individual cells are derived by cell division from one parental cell. One CFU corresponds to ~1000 copies of rRNA.

As used herein, the term "TTime" is the threshold time or time of emergence of signal in a real-time plot of the assay data. TTime values estimate the time at which a particular threshold indicating amplicon production is passed in a real-time amplification reaction. TTime and an algorithm for calculating and using TTime values are described in Light et al., U.S. Pub. No. 2006/0276972, paragraphs [0517] through [0538], the disclosure of which is hereby incorporated by reference herein. A curve fitting procedure is applied to normalized and background-adjusted data. The curve fit is performed for only a portion of the data between a predetermined low bound and high bound. The goal, after finding the curve that fits the data, is to estimate the time corresponding to the point at which the curve or a projection thereof intersects a predefined threshold value. In one embodiment, the threshold for normalized data is 0.11. The high and low bounds are determined empirically as that range over which curves fit to a variety of control data sets exhibit the least variability in the time associated with the given threshold value. For example, in one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve y=mx+b are determined for the fitted curve. With that information, TTime can be determined using the following equation:

$$TTime=(Threshold-b)/m$$

As used herein, the term "relative fluorescence unit" ("RFU") is an arbitrary unit of measurement of fluorescence intensity. RFU varies with the characteristics of the detection means used for the measurement.

As used herein, the term "real-time TMA" refers to single-primer transcription-mediated amplification ("TMA") of target nucleic acid that is monitored by real-time detection means.

The term "about" as used herein in the context of nucleotide positions means the indicated position ±1 nucleotide; or ±2 nucleotides; or ±3 nucleotides; or ±4 nucleotides; or ±5 nucleotides.

BRIEF DESCRIPTION OF THE DRAWINGS

FIG. 2 shows sequences encompassing the Listeria "450" amplification and detection region (corresponding to bp 350-505 of the 16S rRNA of E. coli, Accession No. J01859).

FIG. 3 shows sequences encompassing the Listeria "1275" amplification and detection region (corresponding to bp 1180-1370 of the 16S rRNA of E. coli, Accession No. J01859).

DETAILED DESCRIPTION

Figure 1A:
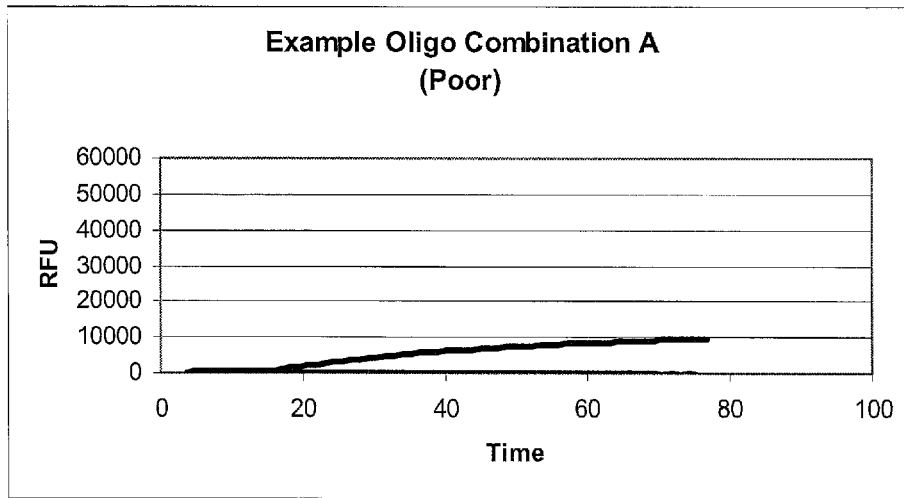
FIGS. 1A-C show generic examples of amplification charts for analyte showing (1A) "Poor", (1B) "Better", and (1C) "Good" assay performance.

In certain aspects and embodiments, the invention relates to compositions, methods and kits for the identification, detection, and/or quantitation of Listeria, which may be present either alone or as a component, large or small, of a homogeneous or heterogeneous mixture of nucleic acids in a sample taken for testing, e.g., for diagnostic testing, for screening of blood products, for microbiological detection in bioprocesses, food, water, industrial or environmental samples, and for other purposes. Specific methods, compositions, and kits as disclosed herein provide improved sensitivity, specificity, or speed of detection in the amplification-based detection of Listeria. Listeria ribosomal RNA is very closely related to rRNA of Brochothrix thermosphacta and Erysipelothrix rhusiopathiae. Accordingly, in certain embodiments of the invention, the Listeria assay identifies rRNA sequences common to nearly all species, subspecies and serovars of the Listeria genus, and differentiates Listeria from other closely related species. A useful region for such differentiation is the 450 region of the 16S rRNA. An alternative region for such differentiation is the 1275 region of the 16S rRNA.

As a result of extensive analyses of amplification oligonucleotides specific for Listeria, the particular region of Listeria corresponding to the region from about 350 to about 505 bp of E. coli (accession no. J01859) 16S rRNA reference sequence, hereinafter referred to as the "450 region", has been identified as a preferred target for amplification-based detection of Listeria. Accordingly, the invention relates to methods of detection of Listeria in a sample of interest, amplification oligonucleotides, compositions, reactions mixtures, kits, and the like.

The Listeria genus assay detects ribosomal RNA sequences specific for known Listeria species. It utilizes real-time TMA technology, where the target-specific sequence is amplified using reverse TMA and a probe is used to detect the amplified products as they are produced. Target detection is performed simultaneously with the amplification and detection of an internal control in order to confirm reliability of the result. The result of the assay consists of the classification of the sample as positive or negative for the presence or absence of *Listeria*. The assay is capable of amplifying more than one *Listeria* species. In some preferred embodiments, two or more *Listeria* species selected from the group consisting of *L. monocytogenes, L. innocua, L. welshimeri, L. ivanovii, L. seeligeri, L. grayi*, and *L. murrayi* are amplified. In other preferred embodiments, all of the species are amplified.

In one embodiment, the sample is a biopharmaceutical process (bioprocess) stream where *Listeria* is a known or suspected contaminant. A "bioprocess," as used herein, refers generally to any process in which living cells or organisms, or components thereof, are present, either intended or unintended. For example, essentially any manufacturing or other process that employs one or more samples or sample streams, at least one of which contains living cells, organisms, or components thereof, or contains such cells, organisms or components as a result of unintended contamination, is considered a bioprocess. In many such processes it is desirable to have the ability to detect, identify and/or control the presence and/or sources of living cells, organisms or components thereof within a process. Using the methods disclosed herein, for example, the presence and/or sources of *Listeria* in one or more bioprocess samples and/or streams may be monitored in a rapid and sensitive fashion.

Target Nucleic Acid/Target Sequence

Target nucleic acids may be isolated from any number of sources based on the purpose of the amplification assay being carried out. Sources of target nucleic acids include, but are not limited to, clinical specimens, e.g., blood, urine, saliva, feces, semen, or spinal fluid, from criminal evidence, from environmental samples, e.g., water or soil samples, from food, from industrial samples, from cDNA libraries, or from total cellular RNA. If necessary, target nucleic acids are made available for interaction with various oligonucleotides. This may include, for example, cell lysis or cell permeabilization to release the target nucleic acid from cells, which then may be followed by one or more purification steps, such as a series of isolation and wash steps. See, e.g., Clark et al., "Method for Extracting Nucleic Acids from a Wide Range of Organisms," U.S. Pat. No. 5,786,208, the contents of which are hereby incorporated by reference herein. This is particularly important where the sample may contain components that can interfere with the amplification reaction, such as, for example, heme present in a blood sample. See Ryder et al., "Amplification of Nucleic Acids from Mononuclear Cells Using Iron Complexing and Other Agents," U.S. Pat. No. 5,639,599, the contents of which are hereby incorporated by reference herein. Methods to prepare target nucleic acids from various sources for amplification are well known to those of ordinary skill in the art. Target nucleic acids may be purified to some degree prior to the amplification reactions described herein, but in other cases, the sample is added to the amplification reaction without any further manipulations.

As will be understood by those of ordinary skill in the art, "unique" sequences are judged from the testing environment. In some embodiments, the sequences recognized by the priming oligonucleotide and/or provider oligonucleotide should be unique in the environment being tested, but need not be unique within the universe of all possible sequences. In other embodiments, the sequences recognized by the detection probe should be unique in the environment being tested, but need not be unique within the universe of all possible sequences. Even though the target sequence may contain a "unique" sequence for recognition by a detection probe, it is not always the case that the priming oligonucleotide and/or provider oligonucleotide are recognizing "unique" sequences. In some embodiments, it may be desirable to choose a target sequence which is common to a family of related organisms. In other situations, a very highly specific target sequence, or a target sequence having at least a highly specific region recognized by the detection probe and amplification oligonucleotides, would be chosen so as to distinguish between closely related organisms.

A target sequence may be of any practical length. A minimal target sequence includes the region which hybridizes to the priming oligonucleotide (or the complement thereof), the region which hybridizes to the hybridizing region of the provider oligonucleotide (or the complement thereof), and a region used for detection, e.g., a region which hybridizes to a detection probe. The region which hybridizes with the detection probe may overlap with or be contained within the region which hybridizes with the priming oligonucleotide (or its complement) or the hybridizing region of the provider oligonucleotide (or its complement). In addition to the minimal requirements, the optimal length of a target sequence depends on a number of considerations, for example, the amount of secondary structure, or self-hybridizing regions in the sequence. Typically, target sequences range from 30 nucleotides in length to about 300 nucleotides in length. The optimal or preferred length may vary under different conditions which can be determined according to the methods described herein.

Nucleic Acid "Identity"

In certain embodiments, a nucleic acid comprises a contiguous base region that is at least 70%; or 75%; or 80%, or 85% or 90%, or 95%; or 100% identical to a contiguous base region of a reference nucleic acid. For short nucleic acids, the degree of identity between a base region of a "query" nucleic acid and a base region of a reference nucleic acid can be determined by manual alignment. "Identity" is determined by comparing just the sequence of nitrogenous bases, irrespective of the sugar and backbone regions of the nucleic acids being compared. Thus, the query:reference base sequence alignment may be DNA:DNA, RNA:RNA, DNA: RNA, RNA:DNA, or any combinations or analogs thereof. Equivalent RNA and DNA base sequences can be compared by converting U's (in RNA) to T's (in DNA).

Oligonucleotides & Primers

An oligonucleotide can be virtually any length, limited only by its specific function in the amplification reaction or in detecting an amplification product of the amplification reaction. However, in certain embodiments, preferred oligonucleotides will contain at least about 10; or 12; or 14; or 16; or 18; or 20; or 22; or 24; or 26; or 28; or 30; or 32; or 34; or 36; or 38; or 40; or 42; or 44; or 46; or 48; or 50; or 52; or 54; or 56 contiguous bases that are complementary to a region of the target nucleic acid sequence or its complementary strand. The contiguous bases are preferably at least about 80%, more preferably at least about 90%, and most preferably completely complementary to the target sequence to which the oligonucleotide binds. Certain preferred oligonucleotides are of lengths generally between about 10-100; or 12-75; or 14-50; or 15-40 bases long and optionally can include modified nucleotides.

Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. As intended by this disclosure, an oligonucleotide does not consist solely of wild-type chromosomal DNA or the in vivo transcription products thereof.

Oligonucleotides may be modified in any way, as long as a given modification is compatible with the desired function of a given oligonucleotide. One of ordinary skill in the art can easily determine whether a given modification is suitable or desired for any given oligonucleotide. Modifications include base modifications, sugar modifications or backbone modifications. Base modifications include, but are not limited to the use of the following bases in addition to adenosine, cytidine, guanosine, thymidine and uridine: C-5 propyne, 2-amino adenine, 5-methyl cytidine, inosine, and dP and dK bases. The sugar groups of the nucleoside subunits may be ribose, deoxyribose and analogs thereof, including, for example, ribonucleosides having a 2'-O-methyl substitution to the ribofuranosyl moiety. See Becker et al., U.S. Pat. No. 6,130,038. Other sugar modifications include, but are not limited to 2'-amino, 2'-fluoro, (L)-alpha-threofuranosyl, and pentopyranosyl modifications. The nucleoside subunits may by joined by linkages such as phosphodiester linkages, modified linkages or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo peptide backbone, such as a 2-aminoethylglycine backbone which couples the nucleobase subunits by means of a carboxymethyl linker to the central secondary amine DNA analogs having a pseudo peptide backbone are commonly referred to as "peptide nucleic acids" or "PNA" and are disclosed by Nielsen et al., "Peptide Nucleic Acids," U.S. Pat. No. 5,539,082. Other linkage modifications include, but are not limited to, morpholino bonds.

Non-limiting examples of oligonucleotides or oligos contemplated herein include nucleic acid analogs containing bicyclic and tricyclic nucleoside and nucleotide analogs (LNAs). See Imanishi et al., U.S. Pat. No. 6,268,490; and Wengel et al., U.S. Pat. No. 6,670,461.) Any nucleic acid analog is contemplated by the present invention provided the modified oligonucleotide can perform its intended function, e.g., hybridize to a target nucleic acid under stringent hybridization conditions or amplification conditions, or interact with a DNA or RNA polymerase, thereby initiating extension or transcription. In the case of detection probes, the modified oligonucleotides must also be capable of preferentially hybridizing to the target nucleic acid under stringent hybridization conditions.

The design and sequence of oligonucleotides depend on their function as described below. Several variables to take into account include: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to initially screen large numbers of potential oligonucleotides.

The 3'-terminus of an oligonucleotide (or other nucleic acid) can be blocked in a variety of ways using a blocking moiety, as described below. A "blocked" oligonucleotide is not efficiently extended by the addition of nucleotides to its 3'-terminus, by a DNA- or RNA-dependent DNA polymerase, to produce a complementary strand of DNA. As such, a "blocked" oligonucleotide cannot be a "primer".

Blocking Moiety

A blocking moiety may be a small molecule, e.g., a phosphate or ammonium group, or it may be a modified nucleotide, e.g., a 3'2' dideoxynucleotide or 3' deoxyadenosine 5'-triphosphate (cordycepin), or other modified nucleotide. Additional blocking moieties include, for example, the use of a nucleotide or a short nucleotide sequence having a 3'-to-5' orientation, so that there is no free hydroxyl group at the 3'-terminus, the use of a 3' alkyl group, a 3' non-nucleotide moiety (see, e.g., Arnold et al., "Non-Nucleotide Linking Reagents for Nucleotide Probes," U.S. Pat. No. 6,031,091, the contents of which are hereby incorporated by reference herein), phosphorothioate, alkane-diol residues, peptide nucleic acid (PNA), nucleotide residues lacking a 3' hydroxyl group at the 3'-terminus, or a nucleic acid binding protein. Preferably, the 3'-blocking moiety comprises a nucleotide or a nucleotide sequence having a 3'-to-5' orientation or a 3' non-nucleotide moiety, and not a 3'2'-dideoxynucleotide or a 3' terminus having a free hydroxyl group. Additional methods to prepare 3'-blocking oligonucleotides are well known to those of ordinary skill in the art.

Priming Oligonucleotide or Primer

A priming oligonucleotide is extended by the addition of covalently bonded nucleotide bases to its 3'-terminus, which bases are complementary to the template. The result is a primer extension product. Suitable and preferred priming oligonucleotides are described herein. Virtually all DNA polymerases (including reverse transcriptases) that are known require complexing of an oligonucleotide to a single-stranded template ("priming") to initiate DNA synthesis, whereas RNA replication and transcription (copying of RNA from DNA) generally do not require a primer. By its very nature of being extended by a DNA polymerase, a priming oligonucleotide does not comprise a 3'-blocking moiety.

Promoter Oligonucleotide/Promoter Sequence

For binding, it was generally thought that such transcriptases required DNA which had been rendered double-stranded in the region comprising the promoter sequence via an extension reaction, however, it has been determined that efficient transcription of RNA can take place even under conditions where a double-stranded promoter is not formed through an extension reaction with the template nucleic acid. The template nucleic acid (the sequence to be transcribed) need not be double-stranded. Individual DNA-dependent RNA polymerases recognize a variety of different promoter sequences, which can vary markedly in their efficiency in promoting transcription. When an RNA polymerase binds to a promoter sequence to initiate transcription, that promoter sequence is not part of the sequence transcribed. Thus, the RNA transcripts produced thereby will not include that sequence.

Terminating Oligonucleotide

A terminating oligonucleotide or "blocker" is designed to hybridize to the target nucleic acid at a position sufficient to achieve the desired 3'-end for the nascent nucleic acid strand. The positioning of the terminating oligonucleotide is flexible depending upon its design. A terminating oligonucleotide may be modified or unmodified. In certain embodiments, terminating oligonucleotides are synthesized with at least one or more 2'-O-methyl ribonucleotides. These modified nucleotides have demonstrated higher thermal stability of complementary duplexes. The 2'-O-methyl ribonucleotides also function to increase the resistance of oligonucleotides to exonucleases, thereby increasing the half-life of the modified oligonucleotides. See, e.g., Majlessi et al. (1988) Nucleic Acids Res. 26, 2224-9, the contents of which are hereby incorporated by reference herein. Other modifications as described elsewhere herein may be utilized in addition to or in place of 2'-O-methyl ribonucleotides. For example, a terminating oligonucleotide may comprise PNA or an LNA. See, e.g., Petersen et al. (2000) *J. Mol. Recognit.* 13, 44-53, the contents of which are hereby incorporated by reference herein. A terminating oligonucleotide typically includes a blocking moiety at its 3'-terminus to prevent extension. A terminating oligonucleotide may also comprise a protein or peptide joined to the oligonucleotide so as to terminate further extension of a nascent nucleic acid chain by a polymerase. Suitable and preferred terminating oligonucleotides are described herein. It is noted that while a terminating oligonucleotide typically or necessarily includes a 3'-blocking moiety, "3'-blocked" oligonucleotides are not necessarily terminating oligonucleotides. Other oligonucleotides as disclosed herein, e.g., provider oligonucleotides and capping oligonucleotides are typically or necessarily 3'-blocked as well.

Extender Oligonucleotide

An extender oligonucleotide hybridizes to a DNA template adjacent to or near the 3'-end of the first region of a promoter oligonucleotide. An extender oligonucleotide preferably hybridizes to a DNA template such that the 5'-terminal base of the extender oligonucleotide is within 3, 2 or 1 bases of the 3'-terminal base of a provider oligonucleotide. Most preferably, the 5'-terminal base of an extender oligonucleotide is adjacent to the 3'-terminal base of a provider oligonucleotide when the extender oligonucleotide and the provider oligonucleotide are hybridized to a DNA template. To prevent extension of an extender oligonucleotide, a 3'-terminal blocking moiety is typically included.

Probe

As would be understood by someone having ordinary skill in the art, a probe comprises an isolated nucleic acid molecule, or an analog thereof, in a form not found in nature without human intervention (e.g., recombined with foreign nucleic acid, isolated, or purified to some extent). Probes may have additional nucleosides or nucleobases outside of the targeted region so long as such nucleosides or nucleobases do not substantially affect hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promoter sequence, a binding site for RNA transcription, a restriction endonuclease recognition site, or may contain sequences which will confer a desired secondary or tertiary structure, such as a catalytic active site or a hairpin structure on the probe, on the target nucleic acid, or both.

The probes preferably include at least one detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particularly preferred embodiment, the label is an acridinium ester. Certain probes as disclosed herein do not include a label. For example, non-labeled "capture" probes may be used to enrich for target sequences or replicates thereof, which may then be detected by a second "detection" probe. See, e.g., Weisburg et al., "Two-Step Hybridization and Capture of a Polynucleotide," U.S. Pat. No. 6,534,273, which is hereby incorporated by reference herein. While detection probes are typically labeled, certain detection technologies do not require that the probe be labeled. See, e.g., Nygren et al., "Devices and Methods for Optical Detection of Nucleic Acid Hybridization," U.S. Pat. No. 6,060,237.

Probes of a defined sequence may be produced by techniques known to those of ordinary skill in the art, such as by chemical synthesis, and by in vitro or in vivo expression from recombinant nucleic acid molecules. Preferably probes are 10 to 100 nucleotides in length, more preferably 12 to 50 bases in length, and even more preferably 12 to 35 bases in length.

Hybridize/Hybridization

Nucleic acid hybridization is the process by which two nucleic acid strands having completely or partially complementary nucleotide sequences come together under predetermined reaction conditions to form a stable, double-stranded hybrid. Either nucleic acid strand may be a deoxyribonucleic acid (DNA) or a ribonucleic acid (RNA) or analogs thereof. Thus, hybridization can involve RNA:RNA hybrids, DNA:DNA hybrids, RNA:DNA hybrids, or analogs thereof. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., Roger L. P. Adams et al., "The Biochemistry Of The Nucleic Acids" ($11^{th}$ ed. 1992).

"Stringent" hybridization assay conditions refer to conditions wherein a specific detection probe is able to hybridize with target nucleic acids over other nucleic acids present in the test sample. It will be appreciated that these conditions may vary depending upon factors including the GC content and length of the probe, the hybridization temperature, the composition of the hybridization reagent or solution, and the degree of hybridization specificity sought. Specific stringent hybridization conditions are provided in the disclosure below.

Nucleic Acid Amplification

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA. The ligase chain reaction (Weiss, R. 1991, Science 254: 1292), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Another method is strand displacement amplification (Walker, G. et al., 1992, Proc. Natl. Acad. Sci. USA 89:392-396; U.S. Pat. Nos. 5,270,184 and 5,455,166), commonly referred to as SDA, which uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315). Other amplification methods include: nucleic acid sequence based amplification (U.S. Pat. No. 5,130,238), commonly referred to as NASBA; one that uses an RNA replicase to amplify the probe molecule itself (Lizardi, P. et al., 1988, BioTechnol. 6: 1197-1202), commonly referred to as Q-β replicase; a transcription-based amplification method (Kwoh, D. et al., 1989, Proc. Natl. Acad. Sci. USA 86:1173-1177); self-sustained sequence replication (Guatelli, J. et al., 1990, Proc. Natl. Acad. Sci. USA 87: 1874-1878); and, transcription-mediated amplification (U.S. Pat. Nos. 5,480,784 and 5,398,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, DC).

In a preferred embodiment, *Listeria* is detected by a transcription-based amplification technique. One preferred transcription-based amplification system is transcription-mediated amplification (TMA), which employs an RNA polymerase to produce multiple RNA transcripts of a target region. Exemplary TMA amplification methods are described in U.S. Pat. Nos. 5,480,784, 5,399,491, 7,374,885, and references cited therein, the contents of which are incorporated herein by reference in their entireties. TMA uses a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In one version of the TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce promoter-primer extension. From an unmodified promoter-primer, reverse transcriptase creates a cDNA copy of the target RNA, while RNase H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNase H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

Another version of TMA uses one primer and one or more additional amplification oligomers to amplify nucleic acids in vitro, making transcripts (amplicons) that indicate the presence of the target sequence in a sample (described in Becker et al., U.S. Pat. No. 7,374,885, the details of which are hereby incorporated by reference herein). Briefly, the single-primer TMA method uses a primer (or "priming oligomer"), a modified promoter oligomer (or "promoter-provider") that is modified to prevent the initiation of DNA synthesis from its 3' end (e.g., by including a 3'-blocking moiety) and, optionally, a binding molecule (e.g., a 3'-blocked extender oligomer) to terminate elongation of a cDNA from the target strand. As referred to herein, a "T7 provider" is a blocked promoter-provider oligonucleotide that provides an oligonucleotide sequence that is recognized by T7 RNA polymerase. This method synthesizes multiple copies of a target sequence and includes the steps of treating a target RNA that contains a target sequence with a priming oligomer and a binding molecule, where the primer hybridizes to the 3' end of the target strand. RT initiates primer extension from the 3' end of the primer to produce a cDNA which is in a duplex with the target strand (e.g., RNA:cDNA). When a binding molecule, such as a 3' blocked extender oligomer, is used in the reaction, it binds to the target nucleic acid adjacent near the 5' end of the target sequence. That is, the binding molecule binds to the target strand next to the 5' end of the target sequence to be amplified. When the primer is extended by DNA polymerase activity of RT to produce cDNA, the 3' end of the cDNA is determined by the position of the binding molecule because polymerization stops when the primer extension product reaches the binding molecule bound to the target strand. Thus, the 3' end of the cDNA is complementary to the 5' end of the target sequence. The RNA:cDNA duplex is separated when RNase (e.g., RNase H of RT) degrades the RNA strand, although those skilled in the art will appreciate that any form of strand separation may be used. Then, the promoter-provider oligomer hybridizes to the cDNA near the 3' end of the cDNA strand. The promoter-provider oligomer includes a 5' promoter sequence for an RNA polymerase and a 3' region complementary to a sequence in the 3' region of the cDNA. The promoter-provider oligomer also has a modified 3' end that includes a blocking moiety that prevents initiation of DNA synthesis from the 3' end of the promoter-provider oligomer. In the promoter-provider:cDNA duplex, the 3'-end of the cDNA is extended by DNA polymerase activity of RT using the promoter oligomer as a template to add a promoter sequence to the cDNA and create a functional double-stranded promoter. An RNA polymerase specific for the promoter sequence then binds to the functional promoter and transcribes multiple RNA transcripts complementary to the cDNA and substantially identical to the target region sequence that was amplified from the initial target strand. The resulting amplified RNA can then cycle through the process again by binding the primer and serving as a template for further cDNA production, ultimately producing many amplicons from the initial target nucleic acid present in the sample. Some embodiments of the single-primer transcription-associated amplification method do not include the binding molecule and, therefore, the cDNA product made from the primer has an indeterminate 3' end, but the amplification steps proceed substantially as described above for all other steps.

Suitable amplification conditions can be readily determined by a skilled artisan in view of the present disclosure. "Amplification conditions" as disclosed herein refer to conditions which permit nucleic acid amplification. Amplification conditions may, in some embodiments, be less stringent than "stringent hybridization conditions" as described herein. Oligonucleotides used in the amplification reactions as disclosed herein may be specific for and hybridize to their intended targets under amplification conditions, but in certain embodiments may or may not hybridize under more stringent hybridization conditions. On the other hand, detection probes generally hybridize under stringent hybridization conditions. While the Examples section infra provides preferred amplification conditions for amplifying target nucleic acid sequences, other acceptable conditions to carry out nucleic acid amplifications could be easily ascertained by someone having ordinary skill in the art depending on the particular method of amplification employed.

The amplification methods as disclosed herein, in certain embodiments, also preferably employ the use of one or more other types of oligonucleotides that are effective for improving the sensitivity, selectivity, efficiency, etc., of the amplification reaction. These may include, for example, terminating oligonucleotides, extender, and/or helper oligonucleotides, and the like.

Target Capture

In certain embodiments, it may be preferred to purify or enrich a target nucleic acid from a sample prior to amplification, for example using a target capture approach. "Target capture" (TC) refers generally to capturing a target polynucleotide onto a solid support, such as magnetically attractable particles, wherein the solid support retains the target polynucleotide during one or more washing steps of the target polynucleotide purification procedure. In this way, the target polynucleotide is substantially purified prior to a subsequent nucleic acid amplification step. Numerous target capture methods are known and suitable for use in conjunction with the methods described herein.

Any support may be used, e.g., matrices or particles free in solution, which may be made of any of a variety of materials, e.g., nylon, nitrocellulose, glass, polyacrylate, mixed polymers, polystyrene, silane polypropylene, or metal. Illustrative examples use a support that is magnetically attractable particles, e.g., monodisperse paramagnetic beads (uniform size. +−0.5%) to which an immobilized probe is joined directly (e.g., via covalent linkage, chelation, or ionic interaction) or indirectly (e.g., via a linker), where the joining is stable during nucleic acid hybridization conditions.

For example, one illustrative approach, as described in U.S. Patent Application Publication No 20060068417, uses at least one capture probe oligonucleotide that contains a target-complementary region and a member of a specific binding pair that attaches the target nucleic acid to an immobilized probe on a capture support, thus forming a capture hybrid that is separated from other sample components before the target nucleic acid is released from the capture support.

In another illustrative method, Weisburg et al., in U.S. Pat. No. 6,110,678, describe a method for capturing a target polynucleotide in a sample onto a solid support, such as magnetically attractable particles, with an attached immobilized probe by using a capture probe and two different hybridization conditions, which preferably differ in temperature only. The two hybridization conditions control the order of hybridization, where the first hybridization conditions allow hybridization of the capture probe to the target polynucleotide, and the second hybridization conditions allow hybridization of the capture probe to the immobilized probe. The method may be used to detect the presence of a target polynucleotide in a sample by detecting the captured target polynucleotide or amplified target polynucleotide.

Another illustrative target capture technique (U.S. Pat. No. 4,486,539) involves a hybridization sandwich technique for capturing and for detecting the presence of a target polynucleotide. The technique involves the capture of the target polynucleotide by a probe bound to a solid support and hybridization of a detection probe to the captured target polynucleotide. Detection probes not hybridized to the target polynucleotide are readily washed away from the solid support. Thus, remaining label is associated with the target polynucleotide initially present in the sample.

Another illustrative target capture technique (U.S. Pat. No. 4,751,177) involves a method that uses a mediator polynucleotide that hybridizes to both a target polynucleotide and to a polynucleotide fixed on a solid support. The mediator polynucleotide joins the target polynucleotide to the solid support to produce a bound target. A labeled probe can be hybridized to the bound target and unbound labeled probe can be washed away from the solid support.

Yet another illustrative target capture technique is described in U.S. Pat. Nos. 4,894,324 and 5,288,609, which describe a method for detecting a target polynucleotide. The method utilizes two single-stranded polynucleotide segments complementary to the same or opposite strands of the target and results in the formation of a double hybrid with the target polynucleotide. In one embodiment, the hybrid is captured onto a support.

In another illustrative target capture technique, EP Pat. Pub. No. 0 370 694, methods and kits for detecting nucleic acids use oligonucleotide primers labeled with specific binding partners to immobilize primers and primer extension products. The label specifically complexes with its receptor which is bound to a solid support.

The above capture techniques are illustrative only, and not limiting. Indeed, essentially any technique available to the skilled artisan may be used provided it is effective for purifying a target nucleic acid sequence of interest prior to amplification.

Nucleic Acid Detection

Essentially any labeling and/or detection system that can be used for monitoring specific nucleic acid hybridization can be used in conjunction to detect *Listeria* amplicons. Many such systems are known and available to the skilled artisan, illustrative examples of which are briefly discussed below.

Detection systems typically employ a detection oligonucleotide of one type or another in order to facilitate detection of the target nucleic acid of interest. Detection may either be direct (i.e., probe hybridized directly to the target) or indirect (i.e., a probe hybridized to an intermediate structure that links the probe to the target). A probe's target sequence generally refers to the specific sequence within a larger sequence which the probe hybridizes specifically. A detection probe may include target-specific sequences and other sequences or structures that contribute to the probe's three-dimensional structure, depending on whether the target sequence is present (e.g., U.S. Pat. Nos. 5,118,801, 5,312,728, 6,835,542, and 6,849,412).

Any of a number of well known labeling systems may be used to facilitate detection. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent or chemiluminescent compound), and fluorescent compound. Preferred embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 6,004,745, 5,656,207 and 5,658,737). Preferred homogeneous detectable labels include chemiluminescent compounds, more preferably acridinium ester ("AE") compounds, such as standard AE or AE derivatives which are well known (U.S. Pat. Nos. 5,656,207, 5,658,737, and 5,948,899). Methods of synthesizing labels, attaching labels to nucleic acid, and detecting signals from labels are well known (e.g., Sambrook et al., Molecular Cloning, A Laboratory Manual, 2nd ed. (Cold Spring Harbor Laboratory Press, Cold Spring Harbor, N.Y., 1989) at Chapter. 10, and U.S. Pat. Nos. 6,414,152, 5,185,439, 5,658,737, 5,656,207, 5,547,842, 5,639,604, 4,581,333, and 5,731,148). Preferred methods of linking an AE compound to a nucleic acid are known (e.g., U.S. Pat. Nos. 5,585,481 and 5,639,604, see column 10, line 6 to column 11, line 3, and Example 8). Preferred AE labeling positions are a probe's central region and near a region of A/T base pairs, at a probe's 3' or 5' terminus, or at or near a mismatch site with a known sequence that the probe should not detect compared to the desired target sequence.

In a preferred embodiment, oligonucleotides exhibiting at least some degree of self-complementarity are desirable to facilitate detection of probe:target duplexes in a test sample without first requiring the removal of unhybridized probe prior to detection. By way of example, when exposed to denaturing conditions, the two complementary regions of a molecular torch, which may be fully or partially complementary, melt, leaving the target binding domain available for hybridization to a target sequence when the predetermined hybridization assay conditions are restored. Molecular torches are designed so that the target binding domain favors hybridization to the target sequence over the target closing domain. The target binding domain and the target closing domain of a molecular torch include interacting labels (e.g., a fluorescent/quencher pair) positioned so that a different signal is produced when the molecular torch is self-hybridized as opposed to when the molecular torch is hybridized to a target nucleic acid, thereby permitting detection of probe:target duplexes in a test sample in the presence of unhybridized probe having a viable label associated therewith. Molecular torches are fully described in U.S. Pat. No. 6,361,945, the disclosure of which is hereby incorporated by reference herein.

Another example of a self-complementary hybridization assay probe that may be used is a structure commonly referred to as a "molecular beacon." Molecular beacons comprise nucleic acid molecules having a target complementary sequence, an affinity pair (or nucleic acid arms) that holds the probe in a closed conformation in the absence of a target nucleic acid sequence, and a label pair that interacts when the probe is in a closed conformation. Hybridization of the molecular beacon target complementary sequence to the target nucleic acid separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are fully described in U.S. Pat. No. 5,925,517, the disclosure of which is hereby incorporated by reference herein. Molecular beacons useful for detecting specific nucleic acid sequences may be created by appending to either end of one of the probe sequences disclosed herein, a first nucleic acid arm comprising a fluorophore and a second nucleic acid arm comprising a quencher moiety. In this configuration, *Listeria*-specific probe sequences may serve as the target-complementary "loop" portion of the resulting molecular beacon.

Molecular beacons are preferably labeled with an interactive pair of detectable labels. Preferred detectable labels interact with each other by FRET or non-FRET energy transfer mechanisms. Fluorescence resonance energy transfer (FRET) involves the radiationless transmission of energy quanta from the site of absorption to the site of its utilization in the molecule or system of molecules by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close such that energy emitted by one label can be received or absorbed by the second label, whether by a FRET or non-FRET mechanism, the two labels are said to be in an "energy transfer relationship." This is the case, for example, when a molecular beacon is maintained in the closed state by formation of a stem duplex and fluorescent emission from a fluorophore attached to one arm of the molecular beacon is quenched by a quencher moiety on the other arm.

Illustrative label moieties for the molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same molecular beacon is in the open state and is stimulated by an appropriate frequency of light, the fluorophore and the quencher moieties are sufficiently separated from each other such that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used, making no attempt to distinguish FRET from non-FRET pairs, include fluorescein/tetramethylrhodamine, IAEDANS/fluorescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2, and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the Black Hole Quencher moieties, which are available from Biosearch Technologies, Inc. (Novato, Calif.).

Synthetic techniques and methods of attaching labels to nucleic acids and detecting labels are well known in the art (see, e.g., Sambrook et al., Molecular Cloning: A Laboratory Manual, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. Nos. 5,185,439 and 6,004,745; Kourilsky et al., U.S. Pat. No. 4,581,333; and, Becker et al., U.S. Pat. No. 5,731,148).

Preferred *Listeria* Oligonucleotides and Oligonucleotide Sets

As described herein, preferred sites for amplifying and detecting *Listeria* nucleic acids as disclosed herein have been found to reside in the 450 region of *Listeria* 16S rRNA. Moreover, particularly preferred oligonucleotides and oligonucleotide sets within this region have been identified for amplifying *Listeria* 16S with improved sensitivity, selectivity and specificity. It will be understood that the oligonucleotides disclosed herein are capable of hybridizing to a *Listeria* target sequence with high specificity and, as a result, are capable of participating in a nucleic acid amplification reaction that can be used to detect the presence and/or levels of one or more *Listeria* species in a sample and distinguish it from the presence of other closely related species.

For example, in one embodiment, the amplification oligonucleotides comprise a first oligonucleotide and a second oligonucleotide, wherein the first and second oligonucleotides target the 450 region of the *Listeria* 16S rRNA with a high degree of specificity.

The amplification oligonucleotides disclosed herein are particularly effective for amplifying a target nucleic acid sequence of *Listeria* in a transcription-based amplification reaction, preferably a real-time transcription-mediated amplification (TMA) reaction.

It will be understood that in addition to the particular T7 provider oligonucleotides and primer oligonucleotides used in the amplification reaction, additional oligonucleotides will also generally be employed in conjunction with the amplification reaction. For example, in certain embodiments, the amplification reactions will also employ the use of one or more of a detection oligonucleotide (e.g., a torch oligonucleotide or an acridinium ester probe), and a blocker oligonucleotide.

Table 1 presents specific examples of T7 Provider oligonucleotides, Primer oligonucleotides, and other ancillary oligonucleotides (e.g., Blocker, Torch, Target Capture, AE probes, and Helper oligonucleotides) that have been identified for the 450 region by the invention.

TABLE 1

Examples of Preferred Oligonucleotides
16S rRNA 450 Region Sequences

| Use | SEQ ID NO: | 450 Region Sequence |
|---|---|---|
| Blocker | SEQ ID NO: 1 | cauugcggaagauucccuac-X |
| Blocker | SEQ ID NO: 2 | cguccauugcggaagauucc-X |
| Blocker | SEQ ID NO: 3 | cuuucguccauugcggaagauuc-X |
| Blocker | SEQ ID NO: 4 | cagacuuucguccauugcggaag-X |
| Blocker | SEQ ID NO: 5 | guugcuccgucagacuuucgucc-X |
| Blocker | SEQ ID NO: 6 | gcggcguugcuccgucagac-X |
| Blocker | SEQ ID NO: 7 | ccuucuucauacacgcgg-X |
| T7 Provider | SEQ ID NO: 8 | AATTTAATACGACTCACTATAGGGAGACAATGGAC GAAAGTCTGACGGAGC-X |

TABLE 1-continued

Examples of Preferred Oligonucleotides
16S rRNA 450 Region Sequences

| Use | SEQ ID NO: | 450 Region Sequence |
| --- | --- | --- |
| T7 Provider | SEQ ID NO: 9 | AATTTAATACGACTCACTATAGGGAGAGGACGAAA GTCTGACGGAGCAACG-X |
| T7 Provider | SEQ ID NO: 10 | AATTTAATACGACTCACTATAGGGAGAGAAAGTCT GACGGAGCAACGCCGC-X |
| T7 Provider | SEQ ID NO: 11 | AATTTAATACGACTCACTATAGGGAGAGTCTGACG GAGCAACGCCGCGTG-X |
| T7 Provider | SEQ ID NO: 12 | AATTTAATACGACTCACTATAGGGAGAGCAACGCC GCGTGTATGAAGAAGG-X |
| T7 Provider | SEQ ID NO: 13 | AATTTAATACGACTCACTATAGGGAGAGCCGCGTG TATGAAGAAGG-X |
| T7 Provider | SEQ ID NO: 14 | AATTTAATACGACTCACTATAGGGAGAGCCGCGTG TGTGAAGAAGG-X |
| T7 Provider | SEQ ID NO: 15 | AATTTAATACGACTCACTATAGGGAGAGAAGGTTT TCGGATCGTAAAG-X |
| Primer | SEQ ID NO: 16 | CAAGCAGTTACTCTTATCCTTGTTCTTCTC |
| Primer | SEQ ID NO: 17 | GGGACAAGCAGTTACTCTTATCC |
| Primer | SEQ ID NO: 18 | CCGTCAAGGGACAAGCAGTTACTC |
| Primer | SEQ ID NO: 19 | GATACCGTCAAGGGACAAGC |
| Primer | SEQ ID NO: 20 | GGTTAGATACCGTCAAGGGACAAGC |
| Primer | SEQ ID NO: 21 | TTAGATACCGTCAAGGGACA |
| Primer | SEQ ID NO: 22 | GGTTAGATACCGTCAAGGGACA |
| Primer | SEQ ID NO: 23 | GGCTTTCTGGTTAGATACCGTC |
| Torch | SEQ ID NO: 24 | cccaguacuuuacgauccgcuggg |
| Torch | SEQ ID NO: 25 | ccggcaguacuuuacgauccgg |
| Torch | SEQ ID NO: 26 | ccggacaguacuuuacgauccgg |
| Torch | SEQ ID NO: 27 | ggcaguuacucuuauccuugcugcc |
| Torch | SEQ ID NO: 28 | gggacaagcaguuacguccc |
| Target Capture | SEQ ID NO: 29 | ccaacuagcuaaugcaccgcgggcTTTAAAAAAAAAAAAA AAAAAAAAAAAAAAA |
| Target Capture | SEQ ID NO: 30 | ccattaccctaccaactagctaatgcaccgTTTAAAAAAAAAAAA AAAAAAAAAAAAAAA |
| Target Capture | SEQ ID NO: 31 | ccauuacccuaccaacuagcuaaugcTTTAAAAAAAAAAAAA AAAAAAAAAAAAAAA |
| Target Capture | SEQ ID NO: 32 | gggccgugucucagucccaguguggTTTAAAAAAAAAAAAA AAAAAAAAAAAAAAA |
| Target Capture | SEQ ID NO: 33 | cugccucccguaggagucgggcTTTAAAAAAAAAAAAAAA AAAAAAAAAAAAA |
| Target Capture | SEQ ID NO: 34 | gcacguaguuagccguggcuuucuggTTTAAAAAAAAAAAAA AAAAAAAAAAAAAAA |
| Target Capture | SEQ ID NO: 35 | gctgctggcacgtagttagccgtgTTTAAAAAAAAAAAAAAAA AAAAAAAAAAAA |
| Target Capture | SEQ ID NO: 36 | gcugcuggcacguaguuagccgugTTTAAAAAAAAAAAAAA AAAAAAAAAAAAAA |

"X" = optional blocking moiety (e.g., reverse 3'-5'-C); lower case n = 2'-O-methyl ribose; upper case N = deoxyribose; 5'-fluorescein ("F") fluorophore and 3'-dabsyl ("D") quencher moieties were attached to the torch oligonucleotides In addition, Table 2 identifies two particularly preferred oligonucleotide sets for use in the compositions, kits and methods as disclosed herein.

TABLE 2

Example of Two Preferred Oligonucleotide Sets 450 Region

| Oligonucleotide Set | Description | Oligonucleotide |
| --- | --- | --- |
| Set #1 | T7 Provider | SEQ ID NO: 13 |
| | Blocker | SEQ ID NO: 6 |
| | Primer | SEQ ID NO: 23 |
| | Torch | SEQ ID NO: 27 |
| Set #2 | T7 Provider | SEQ ID NO: 14 |
| | Blocker | SEQ ID NO: 6 |
| | Primer | SEQ ID NO: 23 |
| | Torch | SEQ ID NO: 27 |

While specifically preferred amplification oligonucleotides derived from the 450 region have been identified, which result in superior assay performance, it will be recognized that other oligonucleotides derived from the 450 region and having insubstantial modifications from those specifically described herein may also be used, provided the same or similar performance objectives are achieved. For example, oligonucleotides derived from the 450 region and useful in the amplification reactions as disclosed herein can have different lengths from those identified herein, provided it does not substantially affect amplification and/or detection procedures. These and other routine and insubstantial modifications to the preferred oligonucleotides can be carried out using conventional techniques, and to the extent such modifications maintain one or more advantages provided herein they are considered within the spirit and scope of the invention.

The general principles as disclosed herein may be more fully appreciated by reference to the following non-limiting Examples.

EXAMPLES

Examples are provided below illustrating certain aspects and embodiments. The examples below are believed to accurately reflect the details of experiments actually performed, however, it is possible that some minor discrepancies may exist between the work actually performed and the experimental details set forth below which do not affect the conclusions of these experiments or the ability of skilled artisans to practice them. Skilled artisans will appreciate that these examples are not intended to limit the invention to the specific embodiments described therein. Additionally, those skilled in the art, using the techniques, materials and methods described herein, could easily devise and optimize alternative amplification systems for carrying out these and related methods while still being within the spirit and scope of the present invention.

Unless otherwise indicated, oligonucleotides and modified oligonucleotides in the following examples were synthesized using standard phosphoramidite chemistry, various methods of which are well known in the art. See e.g., Carruthers, et al., 154 Methods in Enzymology, 287 (1987), the contents of which are hereby incorporated by reference herein. Unless otherwise stated herein, modified nucleotides were 2'-O-methyl ribonucleotides, which were used in the synthesis as their phosphoramidite analogs. For blocked oligonucleotides used in single-primer amplification (Becker et al., U.S. Pat. No. 7,374,885, hereby incorporated by reference herein), the 3'-terminal blocking moiety consisted of a "reversed C" 3'-to-3' linkage prepared using 3'-dimethyltrityl-N-benzoyl-2'-deoxycytidine, 5'-succinoyl-long chain alkylamino-CPG (Glen Research Corporation, Cat. No. 20-0102-01). Molecular torches (see Becker et al., U.S. Pat. No. 6,849,412, hereby incorporated by reference herein) were prepared using a C9 non-nucleotide (triethylene glycol) linker joining region (Spacer Phosphoramidite 9, Glen Research Corporation, Cat. No. 10-1909-xx), 5'-fluorescein ("F") fluorophore and 3'-dabsyl ("D") quencher moieties attached to the oligonucleotide by standard methods.

As set forth in the examples below, analyses of a wide variety of amplification reagents and conditions has led to the development of a highly sensitive and selective amplification process for the detection of *Listeria*.

Example 1

Description of Illustrative Assay Reagents, Equipment and Materials

The following example describes typical assay reagents, protocols, conditions and the like used in the real-time TMA experiments described herein. Unless specified to the contrary, reagent preparation, equipment preparation and assay protocols were performed essentially as set forth below.

*L. monocytogenes*, ATCC 35152, was used as the positive control in all runs. Amplification Reagent was made ahead of time.

A. Reagents and Samples

1. Amplification Reagent. The "Amplification Reagent" or "Amp Reagent" comprised approximate concentrations of the following components: 0.5 mM dATP, 0.5 mM dCTP, 0.5 mM dGTP, 0.5 mM dTTP, 10 mM ATP, 2 mM CTP, 2 mM GTP, 12.7 mM UTP, 30 mM $MgCl_2$, and 33 mM KCl in 50 mM HEPES buffer at pH 7.7. Primers and other oligonucleotides were added to the Amp Reagent.

2. Enzyme Reagent. The "Enzyme Reagent" comprised approximate concentrations of the following components: 1180 RTU/μL Moloney murine leukemia virus ("MMLV") reverse transcriptase ("RT") and 260 PU/μL T7 RNA polymerase in 75 mM HEPES buffer containing 120 mM KCl, 10% TRITON® X-100, 160 mM N-acetyl-L-cysteine, and 1 mM EDTA at pH 7.0, where one RTU of RT activity incorporates 1 nmol of dT into a substrate in 20 minutes at 37° C. and one PU of T7 RNA polymerase activity produces 5 fmol of RNA transcript in 20 minutes at 37° C.

3. Wash Solution. The "Wash Solution" comprised 0.1% (w/v) sodium dodecyl sulfate, 150 mM NaCl and 1 mM EDTA in 10 mM HEPES buffer at pH to 7.5.

4. Target Capture Reagent. The "Target Capture Reagent" (TCR) comprised approximate concentrations of the following components: 60 pmol/mL each of one or more capture probes having a $dT_3dA_{30}$ tail and an optional capture helper probe, 250 to 300 ug/mL paramagnetic oligo-(dT) 14 microparticles (Seradyn), 250 mM HEPES, 100 mM EDTA and 1.88 M LiCl at pH 6.5.

5. Lysis Reagent. The "Lysis Buffer" comprised 1% lithium lauryl sulfate in a buffer containing 100 mM tris, 2.5 mM succinic acid, 10 mM EDTA and 500 mM LiCl at pH 6.5.

6. Target rRNA Samples. rRNA samples were stored in water, 0.1% LiLS or Lysis Reagent prior to use in the experiments described herein.

B. Equipment and Materials

KingFisher® 96 Processor ("KF96")(Thermo Fisher Scientific, Waltham, Mass.).

KingFisher® 96 tip comb for DW magnets (Thermo Fisher Scientific catalog no. 97002534).

KingFisher® 96 KF plate (200 microliters) (Thermo Fisher Scientific catalog no. 97002540).

Hard-Shell Thin-Wall 96-Well Skirted PCR Plate, colored shell/white well ("MJ plate") (catalog numbers: HSP-9615, HSP-9625, HSP-9635, Bio-Rad Laboratories, Hercules, Calif.).

DW 96 plate, V bottom, Polypropylene, sterile 25 pcs/case (Axygen catalog no. P-2ML-SQ-C-S; VWR catalog no. 47749-874; Thermo Fisher Scientific catalog no. 95040460).

eppendorf Thermomixer® R Dry Block Heating and Cooling Shaker with cat. no. 022670565 thermoblock (Eppendorf Corporation, Westbury, N.Y.).

FLUOstar fluorescence microplate reader (BMG Labtech Inc., Cary, N.C.).

PTI® FluoDia® T70 micoplate fluorometer. (Photon Technology International Inc., Birmingham, N.J.)

Example 2

Design and Evaluation of *Listeria* Oligonucleotide Sets

Using a region corresponding to the 450 region of the *E. coli* rRNA sequence (FIG. 2), several T7 Providers, Blockers, Primers, and Torches were designed.

A. Screening

Figure 1B:
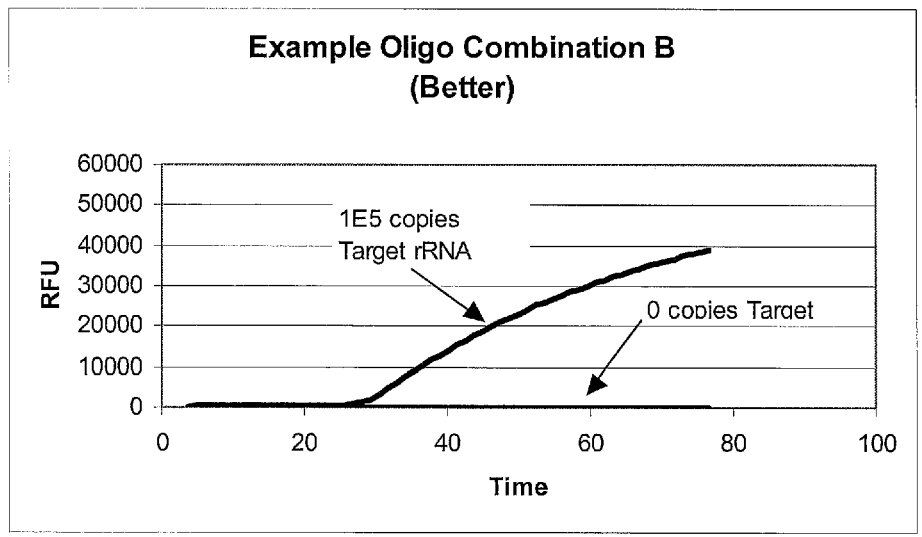
Figure 1C:
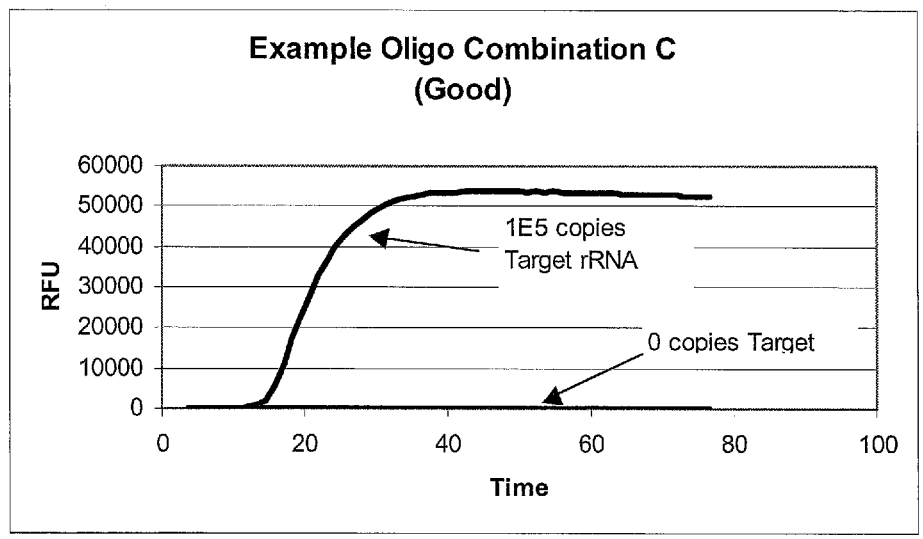

The real-time TMA amplification reactions were performed essentially as follows for simultaneous amplification and detection of analyte and the internal control. A "masterplate" was made that contained T7 Provider (0.5 pmol/μL), Primer (0.5 pmol/μL), and Blocker (0.05 pmol/μL) in reconstituted oligoless amplification reagent (Amp Reagent). Each masterplate well contained 200 μL of a different combination of oligos. For testing, 10 μL of each masterplate well mixture was placed in an MJ plate for amplification. 20 μL of the target nucleic acid in oligoless amplification reagent was added to the plate. Amplification reagent without target was used as the negative control. The amplification plates were covered and placed on a THERMOMIXER apparatus at 60° C. for 10 minutes to anneal the Primer. The plates were cooled to 42° C. on the THERMOMIXER apparatus and incubated for an additional 15 minutes. The plates were then uncovered and 10 μL of enzyme reagent containing detection probe at a concentration of about 1 pmol/μL was added to each amplification reaction well. The plates were covered and mixed on the THERMOMIXER apparatus at 1400 rpm for 1 minute. The plates were immediately placed in a BMG microplate fluorometer and the assay run. Reads were taken every 72 seconds for a total of 63 reads. Two colors were read for each interval. Examples of real-time TMA assay curves are shown in FIG. 1. Assay curve plots and TTime analysis were used to analyze the data.

B. Best Combinations

The best combinations from the screening with *L. monocytogenes* are shown in Table 3. They were chosen on the basis of fluorescence emergence time and maximum fluorescent signal. The oligonucleotide sets were then tested for sensitivity with *L. innocua, L. grayi, L. ivanovii, L. welshimeri, L. murrayi,* and *L. seeligeri*. The oligonucleotide sets were also tested for specificity against *Brochothrix thermosphacta* and *Erysipelothrix rhusiopathiae*. Each target was tested at a target level of 0 or 1E5 copies/assay.

TABLE 3

*Listeria* Oligonucleotide Sets 450 Region

| Oligonucleotide Set | Description | Oligonucleotide |
|---|---|---|
| Set #1 | T7 Provider | SEQ ID NO: 15 |
| | Blocker | SEQ ID NO: 7 |
| | Primer | SEQ ID NO: 23 |
| | Torch | SEQ ID NO: 27 |
| Set #2 | T7 Provider | SEQ ID NO: 12 |
| | Blocker | SEQ ID NO: 5 |
| | Primer | SEQ ID NO: 23 |
| | Torch | SEQ ID NO: 27 |
| Set #3 | T7 Provider | SEQ ID NO: 13 |
| | Blocker | SEQ ID NO: 6 |
| | Primer | SEQ ID NO: 23 |
| | Torch | SEQ ID NO: 27 |
| Set #4 | T7 Provider | SEQ ID NO: 15 |
| | Blocker | SEQ ID NO: 7 |
| | Primer | SEQ ID NO: 21 |
| | Torch | SEQ ID NO: 27 |
| Set #5 | T7 Provider | SEQ ID NO: 12 |
| | Blocker | SEQ ID NO: 5 |
| | Primer | SEQ ID NO: 21 |
| | Torch | SEQ ID NO: 27 |
| Set #6 | T7 Provider | SEQ ID NO: 13 |
| | Blocker | SEQ ID NO: 6 |
| | Primer | SEQ ID NO: 21 |
| | Torch | SEQ ID NO: 27 |
| Set #7 | T7 Provider | SEQ ID NO: 12 |
| | Blocker | SEQ ID NO: 5 |
| | Primer | SEQ ID NO: 23 |
| | Torch | SEQ ID NO: 25 |
| Set #8 | T7 Provider | SEQ ID NO: 13 |
| | Blocker | SEQ ID NO: 6 |
| | Primer | SEQ ID NO: 23 |
| | Torch | SEQ ID NO: 25 |
| Set #9 | T7 Provider | SEQ ID NO: 8 |
| | Blocker | SEQ ID NO: 1 |
| | Primer | SEQ ID NO: 23 |
| | Torch | SEQ ID NO: 25 |
| Set #10 | T7 Provider | SEQ ID NO: 12 |
| | Blocker | SEQ ID NO: 5 |
| | Primer | SEQ ID NO: 16 |
| | Torch | SEQ ID NO: 25 |
| Set #11 | T7 Provider | SEQ ID NO: 13 |
| | Blocker | SEQ ID NO: 6 |
| | Primer | SEQ ID NO: 16 |
| | Torch | SEQ ID NO: 25 |
| Set #12 | T7 Provider | SEQ ID NO: 8 |
| | Blocker | SEQ ID NO: 1 |
| | Primer | SEQ ID NO: 16 |
| | Torch | SEQ ID NO: 25 |

Set #3 was chosen for further evaluation. Set #6 was chosen as the back-up as it only differed in the choice of primer component. The back-up set had no cross-reaction with either of the nearest neighbors but did not perform as well on the *L. grayi* and *L. murrayi* species. Other sets were excluded based on either poor performance to all the *Listeria* sp. Or cross-reaction observed in either *E. rhusiopathiae* or *B. thermosphacta*.

Example 3

Evaluation of Target Capture Integration

Target capture oligos (TCO) for the *Listeria* 16S rRNA were designed to capture target rRNA in regions corresponding from about 230 to 355 and from about 490 to about 525 bp of *E. coli* rRNA. Eight oligos (see Table 1) were designed, synthesized, and tested. Specificity was not built into the TCO's, therefore, they were screened using only *L. monocytogenes* and *L. grayi* RNA. The KINGFISHER 96 processor ("KF96") was used with a large magnet. Target capture was performed using an Axygen deep-well (DW 96)

plate using a 1 mL sample volume. Analysis of the *L. monocytogenes* capture showed that TCOs 2, 3, 6, and 7 were slightly better than TCO 1, 4, 5, and 8. Further evaluation demonstrated that TCOs 2, 3, 6, and 7 all worked acceptably well. Therefore, it was decided to scale-up TCO 2 for the Food Study.

The method of Target Capture with the KINGFISHER 96 processor is summarized in Table 4. In brief, samples were mixed with Lysis Reagent to release target and stabilize rRNA. Target Capture Reagent was added. Ribosomal RNA target was captured and purified on magnetic particles using the KINGFISHER 96 purification system. Particles were resuspended in Amplification Reagent containing 6-carboxyfluoroscein ("FAM")-labeled Torch for analyte and 6-carboxy-tetramethylrhodamine ("TAMRA")-labeled Torch for the internal control. A typical target capture procedure to purify and prepare nucleic acid samples for subsequent amplification was performed essentially as described below. 100 μL of test sample, 50 μL of the TCR containing target capture oligonucleotides, and 1 mL Lysis Reagent were combined and incubated at 60° C. for 15 minutes. The TCR magnetic particles from the treated reaction mixture were captured and washed using the Wash Solution and a suitable magnetic particle washing and separation device (e.g., a magnetic separation rack, a GEN-PROBE Target Capture System (Gen-Probe Cat. No. 5207) or a KINGFISHER magnetic particle processor system (available from Thermo Fisher Scientific). After washing, the magnetic particles were resuspended in 100 μL of the Amplification Reagent.

Specifically, frozen amplification reagent was thawed and lyophilized enzyme reagent was reconstituted. A wash plate was prepared by filling a KF200 plate with 200 μL/well of wash solution. An amp plate was prepared by filling another KF200 plate with 100 μL/well of amplification reagent. Both the amp and wash plates were covered until used. A sample plate was prepared by adding 50 μL non-specific TCR/well into a 2-mL, deep-well 96 plate (Axygen). The target was diluted to the required concentrations in 10 μL lysis solution. One ml of lysis solution was added to each well of the sample plate. With a repeat pipettor, 10 μL of target solution was added to the appropriate deep wells. A deep-well tip-comb was placed in the sample plate. The covers for the wash and amp plates were removed. The KF96 protocol was started and all three plates were placed on the KF96 instrument. The amp plate was placed in position 3, the wash plate in position 2, and the sample (deep-well plate) in position 1. Once the plates were loaded, the KF96 instrument began the target capture step. When the KF96 run was completed, the plates were removed. From the amp plate, 30 μL from each well were removed using a multi-channel pipettor and transferred to an MJ 96-well PCR plate.

TABLE 4

KINGFISHER 96 Program

| Step | Position | Step Description | Action | Beginning | Mix | End |
|---|---|---|---|---|---|---|
| 1 | 1 | Capture | Mix | No action | Very slow- 30 minutes | Collect beads 20 times |
| 2 | 2 | Release to Wash | Wash | Release 30s Slow | 30s Slow | No action |
| 3 | 1 | 2$^{nd}$ Sample Collection | Collect | Collect beads 20 times | No action | No Action |
| 4 | 2 | Release to Wash 2 | Wash | Release 30s Slow | 30s very Slow | Collect beads-count 20 |
| 5 | 3 | Release into Amp Soln | Elution | Release 30s Slow | 30s Slow | No action |

Example 4: Sensitivity, Specificity, and Interference Evaluation

Sensitivity

*L. monocytogenes* (ATCC 35152), *L. grayi* (ATCC 19120), *L. innocua* (ATCC 33090), *L. ivanovii* (F4081), *L. murrayi* (F4076), *L. seeligeri* (F4088), and *L. welshimeri* (F4082) were assayed at 1E5 copies/reaction. Lysis buffer was used as the negative control. Twenty reactions of each were tested using the KINGFISHER 96 instrument for target capture and the BMG reader for detection. From each reaction, one 30 uL replicate was amplified. The positive criterion was 3000 RFU. Nineteen of 20 replicates were to be detected with >95% positivity rate. The results of testing for Sensitivity are shown in Table 5.

TABLE 5

Sensitivity Evaluation

| Organism | ATCC# or Reference # | Copies per Reaction | Number of Reactions | Number of Replicates | Positives | Positivity |
|---|---|---|---|---|---|---|
| *L. grayi* | 19120 | 1E5 | 20 | 1 | 0 | 0% |
| *L. innocua* | 33090 | 1E5 | 20 | 1 | 20 | 100% |

TABLE 5-continued

Sensitivity Evaluation

| Organism | ATCC# or Reference # | Copies per Reaction | Number of Reactions | Number of Replicates | Positives | Positivity |
|---|---|---|---|---|---|---|
| L. ivanovii | F4081 | 1E5 | 20 | 1 | 20 | 100% |
| L. murrayi | F4076 | 1E5 | 20 | 1 | 0 | 0% |
| L. seeligeri | F4088 | 1E5 | 20 | 1 | 20 | 100% |
| L. welshimeri | F4082 | 1E5 | 20 | 1 | 20 | 100% |
| L. monocytogenes* | 35152 | 1E5 | 40 | 1 | 40 | 100% |
| No Target* | NA | 0 | 16 | 1 | 0 | 0% |

*Total of all runs

Initial testing for Sensitivity was considered incomplete since the *L. grayi* and *L. murrayi* were not detected. All other species tested passed yielding a 100% positivity rate. No false positives were observed. *L. grayi* and *L. murrayi* are genotypically identical in the region of amplification. They are also genotypically different from the other species tested by only a one base mismatch in the specific binding region of the T7 provider oligo. Therefore, a redesign was necessary (see Example 5, below).

Specificity

Challenge organisms were tested at 1E5 copies per reaction (approximately 100 CFU) using the KINGFISHER 96 instrument for target capture and the BMG reader for detection. Twenty reactions of all challenge organisms and the negative controls were tested in each plate along with 8 reactions of the positive control. From each reaction one 30 uL replicate was amplified. *L. monocytogenes*, ATCC 35152, was used as a positive control at 1E5 copies per reaction and lysis solution used as a negative control. The positive criterion was 3000 RFU.

A criteria of less than or equal to 10 positives out of 200 reactions (1 out of 20) would meet the goal of ≤5% false positivity rate. The dispersion of any false positives across the 10 organisms was to be considered. Organisms with clustered false positivity (≥4) will be re-tested and further investigated. The results of Specificity evaluation are summarized in Table 6.

TABLE 6

Specificity Evaluation

| Organism | ATCC # | Copies per Reaction | Number of Reactions | Number of Replicates | Positives | Positivity |
|---|---|---|---|---|---|---|
| E. rhusiopathiae | 19414 | 1E5 | 20 | 1 | 0 | 0% |
| B. thermosphacta | 11509 | 1E5 | 20 | 1 | 0 | 0% |
| E. cloacae | 29941 | 1E5 | 20 | 1 | 0 | 0% |
| C. freundii | 33128 | 1E5 | 20 | 1 | 0 | 0% |
| S. flexneri | 12022 | 1E5 | 20 | 1 | 0 | 0% |
| P. mirabilis | 29906 | 1E5 | 20 | 1 | 0 | 0% |
| E. faecalis | 33186 | 1E5 | 20 | 1 | 0 | 0% |
| E. coli | 10798 | 1E5 | 20 | 1 | 0 | 0% |
| C. jejuni | 33560 | 1E5 | 20 | 1 | 0 | 0% |
| S. enteritidis | 10376 | 1E5 | 20 | 1 | 0 | 0% |
| L. monocytogenes (positive)* | 35152 | 1E5 | 32 | 1 | 32 | 100% |
| Negative* | NA | 0 | 80 | 1 | 0 | 0% |

*Total of all runs

Specificity evaluation showed 0% positivity against any of the challenge organisms tested and 100% positivity with the positive control.

Interference

L. monocytogenes, ATCC 35152, was used as the baseline target at 1E5 copies per reaction (approximately 100 CFU). Challenge organisms were spiked into the samples at a concentration of 0 (lysis solution only) or 1E7 copies (approximately 10,000 CFU). Assays were performed using the KINGFISHER 96 processor and the BMG microplate reader. Twelve reactions of all conditions were tested. From each reaction, one 30 uL replicate was amplified. The positive criterion used was 3000 RFU.

Results were to report the reproducibility of positivity in the presence of the nearest neighbor organisms. The dispersion of interference across the organisms tested was to be considered. Organisms exhibiting interference were to be retested and investigated further. The results of Interference evaluation are summarized in Table 7.

TABLE 7

Interference Evaluation

| Organism | ATCC # | Copies per Reaction | Number of Reactions | Number of Replicates | Positives | Positivity |
|---|---|---|---|---|---|---|
| E. rhusiopathiae | 19414 | 1E7 | 12 | 1 | 12 | 100% |
| B. thermosphacta | 11509 | 1E7 | 12 | 1 | 12 | 100% |
| E. cloacae | 29941 | 1E7 | 12 | 1 | 12 | 100% |
| C. freundii | 33128 | 1E7 | 12 | 1 | 12 | 100% |
| S. flexneri | 12022 | 1E7 | 12 | 1 | 12 | 100% |
| P. mirabilis | 29906 | 1E7 | 12 | 1 | 12 | 100% |
| E. faecalis | 33186 | 1E7 | 12 | 1 | 12 | 100% |
| E. coli | 10798 | 1E7 | 12 | 1 | 12 | 100% |
| C. jejuni | 33560 | 1E7 | 12 | 1 | 12 | 100% |
| S. enteritidis | 10376 | 1E7 | 12 | 1 | 12 | 100% |
| L. monocytogenes (positive)* | 35152 | 1E5 | 24 | 1 | 24 | 100% |
| Negative* | NA | 0 | 24 | 1 | 0 | 0% |

*Total of all runs

Interference evaluation showed 100% listeria positivity in the presence of all challenge samples and 100% positivity with the positive control.

Example 5: Redesign of T7 Provider

Additional evaluation of set #3 (Table 3) revealed that the oligonucleotide set did not detect L. grayi and L. murrayi once target capture and the internal control were integrated into the system. An additional T7 provider was designed and evaluated. The goal of the design was to overcome the detrimental effects of the mismatch observed in the L. grayi and L. murrayi species tested while not affecting the detection of other Listeria species/strains. The method of evaluating the redesigned oligo was performed in two sequential experiments. First, the redesigned T7 provider oligo was compared to the control T7 provider using L. grayi and L. monocytogenes. Each T7 provider was tested by itself as well as together in an equal-molar mixture. Once it was determined that the redesigned T7 provider allowed detection of the L. grayi species without loss of detection of the L. monocytogenes, Sensitivity testing was repeated in its entirety. Specificity and Interference evaluation were performed for only the more genetically related organisms, E. rhusiopathiae and B. thermosphacta.

Experiment 1

Amplification reagent containing either the control T7 Provider (SEQ ID NO:13) or the redesigned T7 Provider (SEQ ID NO:14) was formulated. In addition, a third amplification reagent was formulated that contained both T7 providers in an equal-molar ratio. L. monocytogenes (ATCC 35152) and L. grayi (ATCC 19120) were tested with each of the three amplification reagents at levels of 0, 1E3, 1E4, and 1E5 copies per reaction in replicates of 4. All samples were evaluated based on a positive criterion of 3000 RFU.

Experiment 2—Sensitivity, Specificity, and Interference Evaluation

Based on Experiment 1, amplification reagent containing an equal-molar ratio of control T7 provider and redesigned T7 provider was formulated. Evaluation of the Sensitivity was the same as that performed for T7 provider (SEQ ID NO: 13). For Specificity testing, E. rhusiopathiae (ATCC 19414) and B. thermosphacta (ATCC11509) were tested at 1E5 copies per reaction (approximately 100 CFU). Likewise, the same challenge organisms at 1E7 copies per reaction combined with L. monocytogenes (ATCC 35152) at 1E5 copies per reaction were tested to determine any changes in Interference due to the addition of the redesigned T7 provider oligo. Samples evaluated for Sensitivity were performed in replicate reactions of 20, whereas the samples evaluated for Specificity and Interference were performed in replicate reactions of 12. From each reaction, one 30 µL replicate was amplified. All samples were evaluated based on a positive criterion of 3000 RFU.

Results

Experiment 1

The sensitivity results for the T7-Provider redesign are shown in Table 8 and Table 9. Table 9 shows that the oligonucleotide Set 3 with Control T7 Provider (SEQ ID NO:13) showed sensitivity for detecting *L. monocytogenes* nucleic acid at $10^3$ copies per reaction, but required $10^5$ copies per reaction of *L. grayi* nucleic acid to score a positive reaction. Substituting the Redesigned T7 Provider (SEQ ID NO:14) for the Control T7 Provider enhanced sensitivity for detecting *L. grayi* nucleic acid and a mixture of Control and Redesigned T7 Providers gave even better sensitivity.

TABLE 8

*L. grayi* (ATCC 19120)

| Organism | Amplification Reagent | Copies per Reaction | Number of Reactions | Number of Replicates | Positives | Positivity |
|---|---|---|---|---|---|---|
| *L. grayi* | Control T7 Provider (SEQ ID NO: 13) | 0 | 4 | 1 | 0 | 0% |
| | | 1E3 | 4 | 1 | 0 | 0% |
| | | 1E4 | 4 | 1 | 0 | 0% |
| | | 1E5 | 4 | 1 | 4* | 100% |
| | Redesigned T7-Provider (SEQ ID NO: 14) | 0 | 4 | 1 | 0 | 0% |
| | | 1E3 | 4 | 1 | 3 | 75% |
| | | 1E4 | 4 | 1 | 4 | 100% |
| | | 1E5 | 4 | 1 | 4 | 100% |
| | Mixed | 0 | 4 | 1 | 0 | 0% |
| | | 1E3 | 4 | 1 | 4 | 100% |
| | | 1E4 | 4 | 1 | 4 | 100% |
| | | 1E5 | 4 | 1 | 4 | 100% |

*These were very low positives.

TABLE 9

*L. monocytogenes* (ATCC 35152)

| Organism | Amplification Reagent | Copies per Reaction | Number of Reactions | Number of Replicates | Positives | Positivity |
|---|---|---|---|---|---|---|
| *L. monocytogenes* | Control T7 Provider (SEQ ID NO: 13) | 0 | 4 | 1 | 0 | 0% |
| | | 1E3 | 4 | 1 | 4 | 100% |
| | | 1E4 | 4 | 1 | 4 | 100% |
| | | 1E5 | 4 | 1 | 4 | 100% |
| | Redesigned T7-Provider (SEQ ID NO: 14) | 0 | 4 | 1 | 0 | 0% |
| | | 1E3 | 4 | 1 | 4 | 100% |
| | | 1E4 | 4 | 1 | 4 | 100% |
| | | 1E5 | 4 | 1 | 4 | 100% |
| | Mixed | 0 | 4 | 1 | 0 | 0% |
| | | 1E3 | 4 | 1 | 4 | 100% |
| | | 1E4 | 4 | 1 | 4 | 100% |
| | | 1E5 | 4 | 1 | 4 | 100% |

Experiment 2

The results of Experiment 2, with the mixture of T7 Providers from Experiment 1, for Sensitivity, Specificity, and Interference Evaluation are summarized in Table 10, Table 11, and Table 12, respectively.

TABLE 10

Sensitivity Evaluation

| Organism | ATCC# or Reference # | Copies per Reaction | Number of Reactions | Number of Replicates | Positives | Positivity |
|---|---|---|---|---|---|---|
| L. grayi | 19120 | 1E5 | 20 | 1 | 20 | 100% |
| L innocua | 33090 | 1E5 | 20 | 1 | 20 | 100% |
| L. ivanovii | F4081 | 1E5 | 20 | 1 | 20 | 100% |
| L. murrayi | F4076 | 1E5 | 20 | 1 | 20 | 100% |
| L. seeligeri | F4088 | 1E5 | 20 | 1 | 20 | 100% |
| L. welshimeri | F4082 | 1E5 | 20 | 1 | 20 | 100% |
| L. monocytogenes* | 35152 | 1E5 | 40 | 1 | 40 | 100% |
| No Target* | NA | 0 | 16 | 1 | 0 | 0% |

*Total of all runs

TABLE 11

Specificity Evaluation

| Organism | ATCC# | Copies per Reaction | Number of Reactions | Number of Replicates | Positives | Positivity |
|---|---|---|---|---|---|---|
| E. rhusiopathiae | 19414 | 1E5 | 12 | 1 | 0 | 0% |
| B. thermosphacta | 11509 | 1E5 | 12 | 1 | 0 | 0% |
| L. monocytogenes (positive) | 35152 | 1E5 | 12 | 1 | 12 | 100% |
| Negative | NA | 0 | 12 | 1 | 0 | 0% |

TABLE 12

Interference Evaluation

| Organism | ATCC# | Copies per Reaction | Number of Reactions | Number of Replicates | Positives | Positivity |
|---|---|---|---|---|---|---|
| E. rhusiopathiae | 19414 | 1E7 | 12 | 1 | 12 | 100% |
| B. thermosphacta | 11509 | 1E7 | 12 | 1 | 12 | 100% |
| L. monocytogenes (positive) | 35152 | 1E7 | 12 | 1 | 12 | 100% |
| Negative | NA | 0 | 12 | 1 | 0 | 0% |

Evaluation of Sensitivity (Table 10) demonstrated that with a mixture of T7 provider oligos, the L. grayi and L. murrayi that had been missed earlier, were detected with 100% positivity. There was no loss in specificity or increase in interference to the two closest related (genetically) challenge organisms.

These results indicate that the detection of Listeria (all species) can be achieved by the compositions and methods even in the presence of closely related organisms, based upon the characteristics of the real-time TMA data (e.g., the size and shape of RFU curves generated from the real-time TMA reactions).

Example 6: Alternative Regions

Amplification and detection oligonucleotides targeting the nucleotide base region corresponding to bp 1180-1370 of E. coli (accession no. J01859) reference rRNA, hereinafter the "1275 region" (FIG. 3), were prepared for evaluation. These oligonucleotides were designed to be complementary or homologous to Listeria monocytogenes rRNA with as much homology to the other Listeria species in this region.

Table 13 presents sequences of T7 Provider oligonucleotides, Primer oligonucleotides, and other ancillary oligonucleotides (e.g., Blocker, Torch, and Target Capture oligonucleotides) that were designed for the 1275 region by the invention.

TABLE 13

Examples of Preferred Oligonucleotides
16S 1275 Region Sequences

| Use | SEQ ID NO: | 1275 Region Sequence |
|---|---|---|
| Target Capture | SEQ ID NO: 37 | gguguuacaaacucucguggugugacgTTTAAAAAAAAAAAAAAAAAAAAAAAAAAAA |
| Blocker | SEQ ID NO: 38 | gaugauuugacgucauccccaccu-X |
| Blocker | SEQ ID NO: 39 | gcaugaugauuugacgucauc-X |
| Blocker | SEQ ID NO: 40 | cauaaggggcaugaugauuugacg-X |
| Blocker | SEQ ID NO: 41 | cccaggucauaaggggcaugaug-X |
| Blocker | SEQ ID NO: 42 | uguagcccaggucauaagggg-X |
| Blocker | SEQ ID NO: 43 | acguguguagcccaggucauaag-X |
| Blocker | SEQ ID NO: 44 | auccauuguagcacguguguagcc-X |
| T7 Provider | SEQ ID NO: 45 | AATTTAATACGACTCACTATAGGGAGACTTATGACCTGGGCTACACACGTGCTACAATGG-X |
| T7 Provider | SEQ ID NO: 46 | AATTTAATACGACTCACTATAGGGAGAATCATCATGCCCCTTATGACCTGGGCTACA-X |
| T7 Provider | SEQ ID NO: 47 | AATTTAATACGACTCACTATAGGGAGAATCATCATGCCCCTTATGACCTGGGCTACACACG-X |
| T7 Provider | SEQ ID NO: 48 | AATTTAATACGACTCACTATAGGGAGACATGCCCCTTATGACCTGGGCTACACACGTGC-X |
| T7 Provider | SEQ ID NO: 49 | AATTTAATACGACTCACTATAGGGAGACATGCCCCTTATGACCTGGGCTACACACGTGCTA-X |
| T7 Provider | SEQ ID NO: 50 | AATTTAATACGACTCACTATAGGGAGACTGGGCTACACACGTGCTACAATGGATAGT-X |
| T7 Provider | SEQ ID NO: 51 | AATTTAATACGACTCACTATAGGGAGACACACGTGCTACAATGGATAGTACAAAGGG-X |
| T7 Provider | SEQ ID NO: 52 | AATTTAATACGACTCACTATAGGGAGACTACACACGTGCTACAATGGATAGTACAAA-X |
| T7 Provider | SEQ ID NO: 53 | AATTTAATACGACTCACTATAGGGAGACTACACACGTGCTACAATGGATAGTACAAAG-X |
| T7 Provider | SEQ ID NO: 54 | AATTTAATACGACTCACTATAGGGAGACTACACACGTGCTACAATGGATAGTACAAAGG-X |
| T7 Provider | SEQ ID NO: 55 | AATTTAATACGACTCACTATAGGGAGACTACACACGTGCTACAATGGATAGTACAAAGGG-X |
| T7 Provider | SEQ ID NO: 56 | AATTTAATACGACTCACTATAGGGAGACTACACACGTGCTACAATGGATAGTACAAAGGGT-X |
| T7 Provider | SEQ ID NO: 57 | AATTTAATACGACTCACTATAGGGAGACACGTGCTACAATGGATAGTACAAAGGGTCGCG-X |
| T7 Provider | SEQ ID NO: 58 | AATTTAATACGACTCACTATAGGGAGATGGATAGTACAAAGGGTCGCGGAAGCGCGAG-X |
| Primer | SEQ ID NO: 59 | ggcgAGTTGCAGCCTACAATCCGAACUG |
| Primer | SEQ ID NO: 60 | ggcgAGTTGCAGCCTACAATCCGAA |
| Primer | SEQ ID NO: 61 | ggcuTCATGTAGGCGAGTTGCAGCCTACA |
| Primer | SEQ ID NO: 62 | ggcuTCATGTAGGCGAGTTGCAGC |
| Primer | SEQ ID NO: 63 | cgauTCCGGCTTCATGTAGGCGAGTTGCAGC |
| Primer | SEQ ID NO: 64 | cuagCGAUTCCGGCTTCATGTAGGCGAGTTG |
| Primer | SEQ ID NO: 65 | ccacGATTACTAGCGATTCCGGCTTCATGTA |
| Primer | SEQ ID NO: 66 | gaucCACGATTACTAGCGATTCCGGCTT |

TABLE 13-continued

Examples of Preferred Oligonucleotides
16S 1275 Region Sequences

| Use | SEQ ID NO: | 1275 Region Sequence |
|---|---|---|
| Primer | SEQ ID NO: 67 | guggCATGCTGATCCACGATTACTAGCGA |
| Primer | SEQ ID NO: 68 | ggcaTGCTGATCCACGATTACTAGC |
| Primer | SEQ ID NO: 69 | caccGTGGCATGCTGATCCACGATT |
| Torch | SEQ ID NO: 70 | gcuccaccucgcgcuuggagc |
| Torch | SEQ ID NO: 71 | cugggauuagcuccaccucgcgcucccag |
| Torch | SEQ ID NO: 72 | cugggauuagcuccaccucccag |
| Torch | SEQ ID NO: 73 | ggagcuaaucccauaaaacuagcucc |
| Torch | SEQ ID NO: 74 | cggaguaguuuuauggauuagcuccg |
| Torch | SEQ ID NO: 75 | cggaggaauaguuuuaugggauuagcuccg |
| Torch | SEQ ID NO: 76 | cugagaauaguuuuaugggauuagcucccucag |
| Torch | SEQ ID NO: 77 | cgagaauaguuuuaugggauuagcuccucg |
| Torch | SEQ ID NO: 78 | cuaguuuuaugggauuagcuag |
| Torch | SEQ ID NO: 79 | cgagaauaguuuuaugggauuagcucg |
| Torch | SEQ ID NO: 80 | cugagaauaguuuuaugggauuagcucag |
| Torch | SEQ ID NO: 81 | cgaacugagaauaguuuuaugggauuagguucg |
| Torch | SEQ ID NO: 82 | ccgaacugagaauaguucgg |

"X" = optional blocking moiety (e.g., reverse 3'-5'-C); lower case n = 2'-O-methyl ribose; upper case N = deoxyribose; 5'-fluorescein ("F") fluorophore and 3'-dabsyl ("D") quencher moieties were attached to the torch oligonucleotides Screening was performed the same as the screening for the 450 region of the 16S rRNA. *L. grayi* was chosen for the screening. Sequence alignments, see FIG. 3, showed that *L. grayi*, *L. innocua*, *L. seeligeri*, *L. ivanovii* and *L. weishimeri* have similar homologies and mismatches compared to the *L. monocytogenes* sequence in the 1275 region, so it was thought that detection of *L. grayi* would be representative of the ability to detect nucleic acids from the *Listeria* species of interest. All screening was performed at 0 and 1E5 copies/reaction and utilized the BMG reader. The oligonucleotide sets in Table 14 showed the best potential to pick up the *Listeria* genus based on the TTime and the fluorescence signal for *L. grayi*.

TABLE 14

*Listeria* Oligonucleotide Sets 1275 Region

| Oligonucleotide Combination SEQ ID NOs: of Provider: Blocker: Primer: Torch | TTime | RFU Range |
|---|---|---|
| 55:42:59:72 | 18.74 | 36,332 |
| 55:42:65:72 | 17.20 | 33,396 |
| 57:43:64:72 | 17.60 | 36,675 |
| 47:38:64:77 | 18.99 | 32,468 |
| 55:42:65:77 | 17.00 | 41,038 |
| 49:39:59:78 | 19.90 | 36,691 |
| 49:39:64:78 | 17.80 | 36,635 |
| 50:41:64:78 | 18.70 | 32,816 |
| 52:42:68:78 | 18.27 | 34,443 |
| 55:42:63:78 | 19.55 | 34,649 |
| 55:42:64:78 | 15.10 | 34,984 |
| 55:42:65:78 | 16.30 | 33,144 |

TABLE 14-continued

*Listeria* Oligonucleotide Sets 1275 Region

| Oligonucleotide Combination SEQ ID NOs: of Provider: Blocker: Primer: Torch | TTime | RFU Range |
|---|---|---|
| 55:42:68:78 | 15.62 | 31,009 |
| 57:43:64:78 | 16.72 | 40,238 |
| 57:43:65:78 | 16.95 | 30,116 |
| 45:40:64:79 | 19.90 | 52,744 |
| 47:38:68:79 | 16.60 | 39,929 |
| 45:40:65:79 | 18.25 | 46,165 |
| 50:41:66:79 | 18.65 | 41,209 |
| 52:42:65:79 | 19.91 | 40,711 |
| 55:42:65:79 | 17.29 | 42,281 |
| 55:42:67:79 | 19.29 | 37,119 |
| 52:42:64:80 | 18.98 | 42,005 |
| 52:42:65:80 | 18.74 | 31,540 |
| 47:38:64:81 | 18.60 | 34,542 |
| 57:43:67:81 | 18.67 | 30,890 |

In addition, some of the oligonucleotides in Table 13 were redesigned to be more tolerant to the mismatches present in the sequence among the *Listeria* subspecies and are shown in Table 15.

TABLE 15

16S 1275 Region Redesigned Sequences

| Use | SEQ ID NO: | 1275 Region Sequence |
|---|---|---|
| T7 Provider | SEQ ID NO: 83 | AATTTAATACGACTCACTATAGGGAGACTACAC ACGTGCTACAATGGATACTACAAA-X |
| T7 Provider | SEQ ID NO: 84 | AATTTAATACGACTCACTATAGGGAGACTACAC ACGTGCTACAATGGCTAGTACAAA-X |
| T7 Provider | SEQ ID NO: 85 | AATTTAATACGACTCACTATAGGGAGACACGTG CTACAATGGATACTACAAAGGGTCGCG-X |
| T7 Provider | SEQ ID NO: 86 | AATTTAATACGACTCACTATAGGGAGACACGTG CTACAATGGCTAGTACAAAGGGTCGCG-X |
| Primer | SEQ ID NO: 87 | GAGAATAGTTTTATGGATTA |
| Primer | SEQ ID NO: 88 | GAGAATAGTTTTATGGATCA |
| Primer | SEQ ID NO: 89 | GAGAATAGTTTTATGCGATTA |
| Primer | SEQ ID NO: 90 | GAGAATACTTTTATGGATTA |
| Primer | SEQ ID NO: 91 | CTGAGAATAGTTTTATGGATTA |
| Primer | SEQ ID NO: 92 | CTGAGAATAGTTTTATGGATCA |
| Primer | SEQ ID NO: 93 | CTGAGAATAGTTTTATGCGATTA |
| Primer | SEQ ID NO: 94 | CTGAGAATACTTTTATGGATTA |
| Primer | SEQ ID NO: 95 | CCGAACTGAGAATAGTTTTATGGATTA |
| Primer | SEQ ID NO: 96 | ccgaaCTGAGAATAGTTTTATGGATTA |
| Primer | SEQ ID NO: 97 | CCGAACTGAGAATAGTTTTATGGATCA |
| Primer | SEQ ID NO: 98 | ccgaaCTGAGAATAGTTTTATGGATCA |
| Primer | SEQ ID NO: 99 | CCGAACTGAGAATAGTTTTATGCGATTA |
| Primer | SEQ ID NO: 100 | ccgaaCTGAGAATAGTTTTATGCGATTA |
| Primer | SEQ ID NO: 101 | CCGAACTGAGAATACTTTTATGGATTA |
| Primer | SEQ ID NO: 102 | ccgaaCTGAGAATACTTTTATGGATTA |

"X" = optional blocking moiety (e.g., reverse 3'-5'-C); lower case n = 2'-O-methyl ribose; upper case N = deoxyribose; 5'-fluorescein ("F") fluorophore and 3'-dabsyl ("D") quencher moieties were attached to the torch oligonucleotides

Example 7

Food Testing of Spiked Ground Beef and Ice Cream

A small food study was performed using the 450 region Set #3 and TCO 2 (see Examples 2 & 3) oligonucleotides to test ice cream and ground beef as food matrices. The study was conducted in two phases. The first was a pre-study where the dilutions and CFU timing approximated. The second phase of the study evaluated food with spiked *Listeria*. The samples were spiked with 10-20 CFU/25 g of food. The CFU count for the spiking was based on a McFarland 1. Specimens were sampled at 0, 4, 6, 8, 10, and 24 hours. For each point in the time course, the sample was plated for CFU counts, processed for storage and tested with the *Listeria* real-Time TMA assay.

The various steps followed in this study are described below. A McFarland 1 of *Listeria* was made. CFU count confirmation on TSA plates (made dilution to 1E+6 in sterile PBS) was performed. Twenty-five grams of food was weighed and aseptically placed into a STOMACHER bag. Twenty CFU were inoculated directly to 225 mL of Demi-Frazer. The spiked media was poured into the food-containing STOMACHER bag and processed for 2 minutes at 200 rpm. The sample was incubated at 30° C. A 1-mL aliquot was removed (1 aliquot for use in plate count) at times 0, 4, 6, 8, 10, and 24 hours. The sample was plated for CFU counts on selective agar, MOX plates at 3 dilutions, 1 plate/dilution and incubated at 35° C. The remaining five aliquots sampled during a 24-hour period were spun at 12,000×g for 30 seconds. The supernatant was removed and 500 µL of a 50 mM succinate buffer (0.6 M LiCl, 1% LiLS, pH 4.8) was added to the pellet which was then vortexed vigorously for 20 seconds. The sample was heated at >90° C. at least 15 minutes. It was then spun at 12,000×g for 1 minute. The supernatant was transferred to a new labeled tube. Samples were frozen at −70° C. Food controls included: 2 positive and 2 negative for ground beef, 2 positive and 2 negative for plain vanilla ice cream, and 2 positive and 1 negative for the media only pure system.

Pre-Study/CFU Timing:

In the absence of food, spiked *Listeria* (~15 CFU starting inoculum) grew to ~270 CFU/ml after 6 h in broth.

Culture Results:

Using an inoculum of around 24 CFU, the spiked *Listeria* in ground beef grew to around 15 CFU/mL after 8 hours of incubation in Demi-Frazer broth. In spiked ice cream, 70 CFU/mL were observed after 10 hours of incubation in Demi-Frazer broth. The unspiked ground beef was contaminated with *Listeria* spp. or other organisms showing similar cultural characteristics as *Listeria* and had over 6E+4 CFU/mL after 24 hours of incubation. The spiked media without any food sample had around 10 CFU/mL after 10 hours of incubation. By 24 hours, all spiked samples and unspiked ground beef sample in Demi-Frazer broth had >2.8E+4 CFU/mL. The unspiked ice cream and negative media control did not show any *Listeria* growth even after 24 hours incubation in Demi-Frazer broth. CFU counts are shown in Table 16.

TABLE 16

CFU counts at various time points for food spiked with *Listeria monocytogenes* GP803 (24 CFU inoculum)

| Sampling Time (h) | CFU Counts (CFU/mL) | | | | | |
|---|---|---|---|---|---|---|
| | Ground Beef | | Ice Cream | | Media Only | |
| 0 | 0 | 0 | 0 | 0 | 0 | 0 |
| 4 | 0 | 0 | 0 | 0 | 0 | 0 |
| 6 | 0 | 0 | 0 | 0 | 0 | 0 |
| 8 | 15 | 0 | 0 | 0 | 0 | 0 |
| 10 | 40 | 0 | 70 | 0 | 10 | 0 |
| 24 | >4.0E+5 | >6.0E+4 | >1.0E+5 | 0 | >2.8E+4 | 0 |

*Listeria* Real-Time Amplification Results:
Real-Time amplification results are summarized below in Table 17.

TABLE 17

Real-Time Amplification Results

| Time (hours) | Meat Spiked | Meat Unspiked | Ice cream Spiked | Ice cream Unspiked | Media Ctrl Spiked | Media Ctrl Unspiked |
|---|---|---|---|---|---|---|
| 0 | Negative | Negative | Negative | Negative | Negative | Negative |
| 4 | Negative | Negative | Negative | Negative | Negative | Negative |
| 6 | Negative | Negative | Negative | Negative | Negative | Negative |
| 8 | Negative | Negative | Negative | Negative | Negative | Negative |
| 10 | Not tested | Not tested | Not tested | Not tested | Not tested | Not tested |
| 24 | Positive | Low Positive | Positive | Negative | Positive | Negative |

*Listeria* was not detected in any samples until the 24-hour time point. The overall sensitivity of the assay is considered to be between 1E3 and 1E4 copies/reaction (under ideal amplification conditions). The magnitude of interference from the food and media matrices that may cause lower sensitivity than culture is unknown at this time.

SUMMARY

Amplification and detection oligonucleotides targeting the 450 and 1275 regions of *Listeria* nucleic acid, corresponding to *E. coli* 16S rRNA nucleotide base positions at about 350-505 and about 1180-1370, respectively, were designed and synthesized for evaluation.

The 450 region *Listeria* assay was 100% sensitive to all 7 *Listeria* species at 1E+5 copies/reaction (~100 CFU). The *Listeria* assay was 100% specific against 10 non-*Listeria* organisms and *Brochothrix* and *Erysipelothrix*. The limit of detection was 1-10 CFU. The rapid real-time TMA assay can be run in less than four hours, reducing the time needed for testing in food and manufacturing facilities from days to hours.

Oligonucleotides targeting the 1275 region also showed promising results as an alternative to those targeting the 450 region.

Increased assay sensitivity might be achieved by the use of additional amplification and/or detection oligonucleotides designed to amplify and detect the 450 region by itself or to amplify and detect the 450 as well as the 1275 regions of *Listeria*.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

The invention claimed is:

1. A set of oligonucleotides configured to amplify in an amplification reaction a *Listeria* nucleic acid sequence from *L. monocytogenes, L. innocua, L. grayi, L. ivanovii, L. welshimeri, L. murrayi,* and *L. seeligeri* without substantial amplification of a *Brochothrix thermosphacta* nucleic acid or an *Erysipelothrix rhusiopathiae* nucleic acid comprising a first T7 provider oligonucleotide and a first primer oligonucleotide, wherein the first T7 provider oligonucleotide targets a sequence in a first *Listeria* nucleic acid region corresponding to nucleotide positions of about 15-91 of SEQ ID NO: 103; and wherein the first primer oligonucleotide targets a sequence in a second *Listeria* nucleic acid region corresponding to nucleotide positions of about 90-156 of SEQ ID NO: 103.

2. The set of oligonucleotides of claim 1, wherein the first T7 provider oligonucleotide comprises a hybridizing sequence joined at its 5' end to a T7 promoter sequence, wherein the hybridizing sequence is 19-24 nucleobases in length and comprises the hybridizing sequence of SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15.

3. The set of oligonucleotides of claim 2, wherein the first T7 provider oligonucleotide has a nucleobase sequence comprising the nucleobase sequence of SEQ ID NO: 8, SEQ ID NO: 9, SEQ ID NO: 10, SEQ ID NO: 11, SEQ ID NO: 12, SEQ ID NO: 13, SEQ ID NO: 14,-SEQ ID NO: 15, or SEQ ID NO: 12 having a guanine at a position corresponding to nucleotide position 58 of SEQ ID NO: 103.

4. The set of oligonucleotides of claim 2, wherein the primer oligonucleotide has a nucleobase sequence comprising the nucleobase sequence of SEQ ID NO: 23, SEQ ID NO: 21, SEQ ID NO: 16, SEQ ID NO: 17, SEQ ID NO: 18, SEQ ID NO: 19, SEQ ID NO: 20, or SEQ ID NO: 22.

5. The set of oligonucleotides of claim 1, further comprising a second T7 provider oligonucleotide wherein (a) the first T7 provider oligonucleotides has a nucleobase sequence comprising a T7 promoter sequence and the hybridization sequence of SEQ ID NO: 12 or SEQ ID NO: 13 and the second T7 provider oligonucleotide has a nucleobase sequence comprising a T7 promoter sequence and the hybridization sequence of SEQ ID NO: 14.

6. The set of oligonucleotides of claim 5, wherein the primer oligonucleotide has a nucleobase sequence comprising the nucleobase sequence of SEQ ID NO: 23, SEQ ID NO: 21, SEQ ID NO: 16, SEQ ID NO: 17, SEQ ID NO: 18, SEQ ID NO: 19, SEQ ID NO: 20, or SEQ ID: 19.

7. The set of oligonucleotides of claim 6, wherein the primer oligonucleotide has a nucleobase sequence comprising the nucleobase sequence of SEQ ID NO: 23, SEQ ID NO: 21, or SEQ ID NO: 19.

8. The set of oligonucleotides of claim 1, further comprising a second T7 provider oligonucleotide having a nucleobase sequence that overlaps the nucleobase sequence of the first T7 provider oligonucleotide, wherein the first and second T7 provider oligonucleotides differ in one or more nucleobases at a position where there is a mismatch between the nucleobase sequences of one or more *Listeria* species.

9. The set of oligonucleotides of claim 8, wherein the first or second T7 provider oligonucleotide has a nucleobase sequence comprising a T7 promoter sequence and the hybridization sequence of SEQ ID NO: 12, SEQ ID NO: 13, or SEQ ID NO: 14.

10. The set of oligonucleotides of claim 8, wherein the first or second T7 provider oligonucleotide has a nucleobase sequence consisting of the nucleobase sequence of SEQ ID NO: 12 or SEQ ID NO: 13.

11. The set of oligonucleotides of claim 8, wherein the first or second T7 provider oligonucleotides has a nucleobase sequence consisting of the nucleobase sequence of SEQ ID NO: 14 or SEQ ID NO: 12 having a guanine at the position corresponding to nucleotide position 58 of SEQ ID NO: 103.

12. The set of oligonucleotides of claim 8, wherein the primer oligonucleotide has a nucleobase sequence comprising the nucleobase sequence of SEQ ID NO: 23, SEQ ID NO: 21, or SEQ ID NO: 19.

13. The set of oligonucleotides of claim 8, wherein the first T7 provider oligonucleotide comprises an adenine at a nucleobase position that is complementary to a nucleobase position in a *Listeria* nucleic acid sequence corresponding to nucleobase position 58 of SEQ ID NO: 103, and the second T7 provider oligonucleotide comprises a guanine at the nucleobase position that is complementary to the nucleobase position in a *Listeria* nucleic acid sequence corresponding to nucleobase position 58 of SEQ ID NO: 103.

14. The set of oligonucleotides of claim 13, wherein the first T7 provider oligonucleotide has a nucleobase sequence comprising a T7 promoter sequence and the hybridization sequence of SEQ ID NO: 12 or SEQ ID NO: 13 and the second T7 provider oligonucleotide has a nucleobase sequence comprising a T7 promoter sequence and the hybridization sequence of SEQ ID NO: 14.

15. The set of oligonucleotides of claim 14, wherein the primer oligonucleotide has a nucleobase sequence comprising the nucleobase sequence of SEQ ID NO: 23, SEQ ID NO: 21, or SEQ ID NO: 19.

16. A set of oligonucleotides for detecting a *Listeria* nucleic acid sequence in a sample comprising a T7 provider oligonucleotide, a primer oligonucleotide, and a detection oligonucleotide, wherein the T7 provider oligonucleotide and the primer oligonucleotide are configured amplify in an amplification reaction a nucleic acid sequence from *L. monocytogenes, L. innocua, L. grayi, L. ivanovii, L. welshimeri, L. murrayi*, and *L. seeligeri* without substantial amplification of a *Brochothrix thermosphacta* nucleic acid or an *Erysipelothrix rhusiopathiae* nucleic acid, wherein the first T7 provider oligonucleotide targets a sequence in a first *Listeria* nucleic acid region corresponding to nucleotide positions of about 15-91 of SEQ ID NO: 103, and wherein the first primer oligonucleotide targets a sequence in a second *Listeria* nucleic acid region corresponding to nucleotide positions of about 90-156 of SEQ ID NO: 103.

17. The set of oligonucleotides of claim 16, wherein the detection oligonucleotide is a molecular torch oligonucleotide having a nucleobase sequence selected from the group consisting of SEQ ID NO: 24, SEQ ID NO: 25, SEQ ID NO: 26, SEQ ID NO: 27, SEQ ID NO: 28, and a complement thereof.

18. The set of oligonucleotides of claim 1, further comprising a blocker oligonucleotide having a nucleobase sequence selected from the group consisting of SEQ ID NO: 1, SEQ ID NO: 5, SEQ ID NO: 6, and SEQ ID NO: 7.

19. The set of oligonucleotides of claim 1, further comprising a target capture oligonucleotide having a nucleobase sequence selected from the group consisting of SEQ ID NO: 29, SEQ ID NO: 30, SEQ ID NO: 31, SEQ ID NO: 32, SEQ ID NO: 33, SEQ ID NO: 34, SEQ ID NO: 35, and SEQ ID NO: 36.

20. The set of oligonucleotides of claim 16, further comprising a helper oligonucleotide.

\* \* \* \* \*

UNITED STATES PATENT AND TRADEMARK OFFICE
CERTIFICATE OF CORRECTION

PATENT NO. : 11,198,913 B2
APPLICATION NO. : 16/663642
DATED : December 14, 2021
INVENTOR(S) : Reshatoff et al.

It is certified that error appears in the above-identified patent and that said Letters Patent is hereby corrected as shown below:

On the Title Page

Item (56) In section "Other Publications", Column 2, Line 15 delete "16S" and insert --"16S-- and delete "foods," and insert --foods,"--

In the Specification

Column 1, Line 9 delete "2017" and insert --2017, issued as U.S. Pat. No. 10,501,812,--

Column 1, Line 22 delete "reference" and insert --reference.--

Column 2, Line 9 delete "Torch" and insert --torch--

Column 9, Line 24 delete "minimized Thus," and insert --minimized. Thus,--

Column 15, Line 23 delete "may by" and insert --may be--

Column 15, Line 35 delete "amine DNA" and insert --amine. DNA--

Column 15, Line 44 delete "See" and insert --(See--

Column 23, Line 18 delete "signal." and insert --signal).--

Columns 27-28, below Table 1, Line 1 delete "(e g.," and insert --(e.g.,--

Column 31, Line 19 delete "micoplate" and insert --microplate.--

Column 33, Lines 13-14 delete "6-carboxyfluoroscein" and insert --6-carboxyfluorescein--

Column 33, Line 25 delete "rack," and insert --rack),--

Signed and Sealed this
     Twenty-ninth Day of March, 2022

Drew Hirshfeld
      *Performing the Functions and Duties of the*
   *Under Secretary of Commerce for Intellectual Property and*
   *Director of the United States Patent and Trademark Office*

CERTIFICATE OF CORRECTION (continued)
U.S. Pat. No. 11,198,913 B2

Columns 41-42, in table 10, under "Organism", Line 2 delete "*L innocua*" and insert --*L. innocua*--

Column 50, Line 27 delete "containing"," and insert --"containing",--

In the Claims

Column 101, Claim 3, Line 60 delete "14,-SEQ ID NO: 15" and insert --14, SEQ ID NO: 15--

Column 102, Claim 6, Line 45 delete "or SEQ IDS: 19" and insert --or SEQ ID NO: 22--

Column 104, Claim 16, Line 1 delete "configured amplify" and insert --configured to amplify--

SEQUENCE LISTING

```
<160> NUMBER OF SEQ ID NOS: 122

<210> SEQ ID NO 1
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
```

```
<220> FEATURE:
<221> NAME/KEY: modified_base
<222> LOCATION: (20)..(20)
<223> OTHER INFORMATION: Blocking Moiety

<400> SEQUENCE: 1
cauugcggaa gauucccuac                                                    20

<210> SEQ ID NO 2
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (20)..(20)
<223> OTHER INFORMATION: Blocking Moiety

<400> SEQUENCE: 2
cguccauugc ggaagauucc                                                    20

<210> SEQ ID NO 3
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (23)..(23)
<223> OTHER INFORMATION: Blocking Moiety

<400> SEQUENCE: 3
cuuucgucca uugcggaaga uuc                                                23

<210> SEQ ID NO 4
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (23)..(23)
<223> OTHER INFORMATION: Blocking Moiety

<400> SEQUENCE: 4
cagacuuucg uccauugcgg aag                                                23

<210> SEQ ID NO 5
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (23)..(23)
```

<223> OTHER INFORMATION: Blocking Moiety

<400> SEQUENCE: 5
guugcuccgu cagacuuucg ucc                                           23

<210> SEQ ID NO 6
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (20)..(20)
<223> OTHER INFORMATION: Blocking Moiety

<400> SEQUENCE: 6
gcggcguugc uccgucagac                                               20

<210> SEQ ID NO 7
<211> LENGTH: 18
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (18)..(18)
<223> OTHER INFORMATION: Blocking Moiety

<400> SEQUENCE: 7
ccuucuucau acacgcgg                                                 18

<210> SEQ ID NO 8
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 8
aatttaatac gactcactat agggagacaa tggacgaaag tctgacggag c             51

<210> SEQ ID NO 9
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 9
aatttaatac gactcactat agggagagga cgaaagtctg acggagcaac g        51

<210> SEQ ID NO 10
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 10
aatttaatac gactcactat agggagagaa agtctgacgg agcaacgccg c        51

<210> SEQ ID NO 11
<211> LENGTH: 50
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (50)..(50)
<223> OTHER INFORMATION: Blocking Moiety

<400> SEQUENCE: 11
aatttaatac gactcactat agggagagtc tgacggagca acgccgcgtg          50

<210> SEQ ID NO 12
<211> LENGTH: 51
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (51)..(51)
<223> OTHER INFORMATION: Blocking Moiety

<400> SEQUENCE: 12
aatttaatac gactcactat agggagagca acgccgcgtg tatgaagaag g        51

<210> SEQ ID NO 13
<211> LENGTH: 46
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (46)..(46)
<223> OTHER INFORMATION: Blocking Moiety

<400> SEQUENCE: 13
aatttaatac gactcactat agggagagcc gcgtgtatga agaagg              46

<210> SEQ ID NO 14
<211> LENGTH: 46
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (46)..(46)
<223> OTHER INFORMATION: Blocking Moiety

<400> SEQUENCE: 14
aatttaatac gactcactat agggagagcc gcgtgtgtga agaagg        46

<210> SEQ ID NO 15
<211> LENGTH: 48
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (48)..(48)
<223> OTHER INFORMATION: Blocking Moiety

<400> SEQUENCE: 15
aatttaatac gactcactat agggagagaa ggttttcgga tcgtaaag        48

<210> SEQ ID NO 16
<211> LENGTH: 30
<212> TYPE: DNA
<213> ORGANISM: Artificial
<220> FEATURE:
<223> OTHER INFORMATION: Amplification and Detection Oligonucleotide

<400> SEQUENCE: 16
caagcagtta ctcttatcct tgttcttctc        30

<210> SEQ ID NO 17
<211> LENGTH: 23
<212> TYPE: DNA
<213> ORGANISM: Artificial
<220> FEATURE:
<223> OTHER INFORMATION: Amplification and Detection Oligonucleotide

<400> SEQUENCE: 17
gggacaagca gttactctta tcc        23

<210> SEQ ID NO 18
<211> LENGTH: 24
<212> TYPE: DNA
<213> ORGANISM: Artificial
<220> FEATURE:
<223> OTHER INFORMATION: Amplification and Detection Oligonucleotide

<400> SEQUENCE: 18
ccgtcaaggg acaagcagtt actc        24

<210> SEQ ID NO 19
<211> LENGTH: 20
<212> TYPE: DNA
<213> ORGANISM: Artificial

```
<220> FEATURE:
<223> OTHER INFORMATION: Amplification and Detection Oligonucleotide

<400> SEQUENCE: 19
gataccgtca agggacaagc                                                    20

<210> SEQ ID NO 20
<211> LENGTH: 25
<212> TYPE: DNA
<213> ORGANISM: Artificial
<220> FEATURE:
<223> OTHER INFORMATION: Amplification and Detection Oligonucleotide

<400> SEQUENCE: 20
ggttagatac cgtcaaggga caagc                                              25

<210> SEQ ID NO 21
<211> LENGTH: 20
<212> TYPE: DNA
<213> ORGANISM: Artificial
<220> FEATURE:
<223> OTHER INFORMATION: Amplification and Detection Oligonucleotide

<400> SEQUENCE: 21
ttagataccg tcaagggaca                                                    20

<210> SEQ ID NO 22
<211> LENGTH: 22
<212> TYPE: DNA
<213> ORGANISM: Artificial
<220> FEATURE:
<223> OTHER INFORMATION: Amplification and Detection Oligonucleotide

<400> SEQUENCE: 22
ggttagatac cgtcaaggga ca                                                 22

<210> SEQ ID NO 23
<211> LENGTH: 22
<212> TYPE: DNA
<213> ORGANISM: Artificial
<220> FEATURE:
<223> OTHER INFORMATION: Amplification and Detection Oligonucleotide

<400> SEQUENCE: 23
ggctttctgg ttagataccg tc                                                 22

<210> SEQ ID NO 24
<211> LENGTH: 24
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 24
cccaguacuu uacgauccgc uggg                                               24

<210> SEQ ID NO 25
<211> LENGTH: 22
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
```

```
<223> OTHER INFORMATION: 2'-O-methyl ribose

<400> SEQUENCE: 25
ccggcaguac uuuacgaucc gg                                                  22

<210> SEQ ID NO 26
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 26
ccggacagua cuuuacgauc cgg                                                 23

<210> SEQ ID NO 27
<211> LENGTH: 25
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 27
ggcaguuacu cuuauccuug cugcc                                               25

<210> SEQ ID NO 28
<211> LENGTH: 20
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 28
gggacaagca guuacguccc                                                     20

<210> SEQ ID NO 29
<211> LENGTH: 57
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(24)
<223> OTHER INFORMATION: 2'-O-methyl ribose

<400> SEQUENCE: 29
ccaacuagcu aaugcaccgc gggctttaaa aaaaaaaaa aaaaaaaaa aaaaaaa              57

<210> SEQ ID NO 30
<211> LENGTH: 63
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(30)
<223> OTHER INFORMATION: 2'-O-methyl ribose
```

<400> SEQUENCE: 30
ccattaccct accaactagc taatgcaccg tttaaaaaaa aaaaaaaaaa aaaaaaaaaa    60
aaa    63

<210> SEQ ID NO 31
<211> LENGTH: 59
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(26)
<223> OTHER INFORMATION: 2'-O-methyl ribose

<400> SEQUENCE: 31
ccauuacccu accaacuagc uaaugcuuua aaaaaaaaaa aaaaaaaaaa aaaaaaaa    59

<210> SEQ ID NO 32
<211> LENGTH: 58
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(25)
<223> OTHER INFORMATION: 2'-O-methyl ribose

<400> SEQUENCE: 32
gggccguguc ucagucccag uguggtttaa aaaaaaaaaa aaaaaaaaaa aaaaaaa    58

<210> SEQ ID NO 33
<211> LENGTH: 56
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(23)
<223> OTHER INFORMATION: 2'-O-methyl ribose

<400> SEQUENCE: 33
cugccucccg uaggagucug ggctttaaaa aaaaaaaaaa aaaaaaaaaa aaaaaa    56

<210> SEQ ID NO 34
<211> LENGTH: 59
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(26)
<223> OTHER INFORMATION: 2'-O-methyl ribose

<400> SEQUENCE: 34
gcacguaguu agccguggcu uucuggttta aaaaaaaaaa aaaaaaaaaa aaaaaaaa    59

<210> SEQ ID NO 35
<211> LENGTH: 57
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature

```
<222> LOCATION: (1)..(24)
<223> OTHER INFORMATION: 2'-O-methyl ribose

<400> SEQUENCE: 35
gctgctggca cgtagttagc cgtgtttaaa aaaaaaaaaa aaaaaaaaaa aaaaaaa          57

<210> SEQ ID NO 36
<211> LENGTH: 57
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(24)
<223> OTHER INFORMATION: 2'-O-methyl ribose

<400> SEQUENCE: 36
gcugcuggca cguaguuagc cgugtttaaa aaaaaaaaaa aaaaaaaaaa aaaaaaa          57

<210> SEQ ID NO 37
<211> LENGTH: 60
<212> TYPE: DNA
<213> ORGANISM: Artificial
<220> FEATURE:
<223> OTHER INFORMATION: Target Capture DNA-RNA Hybrid Oligonucleotide
<220> FEATURE:
<221> NAME/KEY: misc_feature
<222> LOCATION: (1)..(27)
<223> OTHER INFORMATION: 2'-O-methyl ribose

<400> SEQUENCE: 37
gguguuacaa acucucgugg ugugacgttt aaaaaaaaaa aaaaaaaaaa aaaaaaaaaa       60

<210> SEQ ID NO 38
<211> LENGTH: 24
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (24)..(24)
<223> OTHER INFORMATION: Blocking Moiety

<400> SEQUENCE: 38
gaugauuuga cgucaucccc accu                                              24

<210> SEQ ID NO 39
<211> LENGTH: 21
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (21)..(21)
<223> OTHER INFORMATION: Blocking Moiety

<400> SEQUENCE: 39
gcaugaugau uugacgucau c                                                 21

<210> SEQ ID NO 40
```

```
<211> LENGTH: 24
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (24)..(24)
<223> OTHER INFORMATION: Blocking Moiety

<400> SEQUENCE: 40
cauaaggggc augaugauuu gacg                                              24

<210> SEQ ID NO 41
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (23)..(23)
<223> OTHER INFORMATION: Blocking Moiety

<400> SEQUENCE: 41
cccaggucau aaggggcaug aug                                               23

<210> SEQ ID NO 42
<211> LENGTH: 21
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (21)..(21)
<223> OTHER INFORMATION: Blocking Moiety

<400> SEQUENCE: 42
uguagcccag gucauaaggg g                                                 21

<210> SEQ ID NO 43
<211> LENGTH: 23
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (23)..(23)
<223> OTHER INFORMATION: Blocking Moiety

<400> SEQUENCE: 43
acguguguag cccaggucau aag                                               23

<210> SEQ ID NO 44
<211> LENGTH: 24
<212> TYPE: RNA
<213> ORGANISM: Artificial
```

<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
<220> FEATURE:
<221> NAME/KEY: modified_base
<222> LOCATION: (24)..(24)
<223> OTHER INFORMATION: Blocking Moiety

<400> SEQUENCE: 44
auccauugua gcacgugugu agcc                                    24

<210> SEQ ID NO 45
<211> LENGTH: 60
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (60)..(60)
<223> OTHER INFORMATION: Blocking Moiety

<400> SEQUENCE: 45
aatttaatac gactcactat agggagactt atgacctggg ctacacacgt gctacaatgg    60

<210> SEQ ID NO 46
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 46
aatttaatac gactcactat agggagaatc atcatgcccc ttatgacctg ggctaca       57

<210> SEQ ID NO 47
<211> LENGTH: 61
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (61)..(61)
<223> OTHER INFORMATION: Blocking Moiety

<400> SEQUENCE: 47
aatttaatac gactcactat agggagaatc atcatgcccc ttatgacctg ggctacacac    60
g                                                                    61

<210> SEQ ID NO 48
<211> LENGTH: 59
<212> TYPE: DNA
<213> ORGANISM: Artificial
<220> FEATURE:

<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (59)..(59)
<223> OTHER INFORMATION: Blocking Moiety

<400> SEQUENCE: 48
aatttaatac gactcactat agggagacat gccccttatg acctgggcta cacacgtgc    59

<210> SEQ ID NO 49
<211> LENGTH: 61
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (61)..(61)
<223> OTHER INFORMATION: Blocking Moiety

<400> SEQUENCE: 49
aatttaatac gactcactat agggagacat gccccttatg acctgggcta cacacgtgct    60
a                                                                    61

<210> SEQ ID NO 50
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 50
aatttaatac gactcactat agggagactg ggctacacac gtgctacaat ggatagt    57

<210> SEQ ID NO 51
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 51
aatttaatac gactcactat agggagacac acgtgctaca atggatagta caaaggg    57

<210> SEQ ID NO 52
<211> LENGTH: 57
<212> TYPE: DNA
<213> ORGANISM: Artificial
<220> FEATURE:
<223> OTHER INFORMATION: Amplification and Detection Oligonucleotide

```
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 52
aatttaatac gactcactat agggagacta cacacgtgct acaatggata gtacaaa            57

<210> SEQ ID NO 53
<211> LENGTH: 58
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (58)..(58)
<223> OTHER INFORMATION: Blocking Moiety

<400> SEQUENCE: 53
aatttaatac gactcactat agggagacta cacacgtgct acaatggata gtacaaag           58

<210> SEQ ID NO 54
<211> LENGTH: 59
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (59)..(59)
<223> OTHER INFORMATION: Blocking Moiety

<400> SEQUENCE: 54
aatttaatac gactcactat agggagacta cacacgtgct acaatggata gtacaaagg          59

<210> SEQ ID NO 55
<211> LENGTH: 60
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (60)..(60)
<223> OTHER INFORMATION: Blocking Moiety

<400> SEQUENCE: 55
aatttaatac gactcactat agggagacta cacacgtgct acaatggata gtacaaaggg         60

<210> SEQ ID NO 56
<211> LENGTH: 61
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
```

<220> FEATURE:
<221> NAME/KEY: modified_base
<222> LOCATION: (61)..(61)
<223> OTHER INFORMATION: Blocking Moiety

<400> SEQUENCE: 56
aatttaatac gactcactat agggagacta cacacgtgct acaatggata gtacaaaggg    60
t                                                                   61

<210> SEQ ID NO 57
<211> LENGTH: 60
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (60)..(60)
<223> OTHER INFORMATION: Blocking Moiety

<400> SEQUENCE: 57
aatttaatac gactcactat agggagacac gtgctacaat ggatagtaca aagggtcgcg    60

<210> SEQ ID NO 58
<211> LENGTH: 58
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (58)..(58)
<223> OTHER INFORMATION: Blocking Moiety

<400> SEQUENCE: 58
aatttaatac gactcactat agggagatgg atagtacaaa gggtcgcgga agcgcgag     58

<210> SEQ ID NO 59
<211> LENGTH: 28
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 59
ggcgagttgc agcctacaat ccgaacug                                      28

<210> SEQ ID NO 60
<211> LENGTH: 25
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl ribose

```
<400> SEQUENCE: 60
ggcgagttgc agcctacaat ccgaa                                              25

<210> SEQ ID NO 61
<211> LENGTH: 29
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 61
ggcutcatgt aggcgagttg cagcctaca                                          29

<210> SEQ ID NO 62
<211> LENGTH: 24
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 62
ggcutcatgt aggcgagttg cagc                                               24

<210> SEQ ID NO 63
<211> LENGTH: 31
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 63
cgautccggc ttcatgtagg cgagttgcag c                                       31

<210> SEQ ID NO 64
<211> LENGTH: 31
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 64
cuagcgautc cggcttcatg taggcgagtt g                                       31

<210> SEQ ID NO 65
<211> LENGTH: 31
<212> TYPE: DNA
<213> ORGANISM: Artificial
<220> FEATURE:
<223> OTHER INFORMATION: Amplification and Detection DNA-RNA Hybrid
```

-continued

Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 65
ccacgattac tagcgattcc ggcttcatgt a                                      31

<210> SEQ ID NO 66
<211> LENGTH: 28
<212> TYPE: DNA
<213> ORGANISM: Artificial
<220> FEATURE:
<223> OTHER INFORMATION: Amplification and Detection DNA-RNA Hybrid
    Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 66
gauccacgat tactagcgat tccggctt                                          28

<210> SEQ ID NO 67
<211> LENGTH: 29
<212> TYPE: DNA
<213> ORGANISM: Artificial
<220> FEATURE:
<223> OTHER INFORMATION: Amplification and Detection DNA-RNA Hybrid
    Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 67
guggcatgct gatccacgat tactagcga                                         29

<210> SEQ ID NO 68
<211> LENGTH: 25
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 68
ggcatgctga tccacgatta ctagc                                             25

<210> SEQ ID NO 69
<211> LENGTH: 25
<212> TYPE: DNA
<213> ORGANISM: Artificial
<220> FEATURE:
<223> OTHER INFORMATION: Amplification and Detection DNA-RNA Hybrid
    Oligonucleotide
<220> FEATURE:
<221> NAME/KEY: misc_feature
<222> LOCATION: (1)..(4)
<223> OTHER INFORMATION: 2'-O-methyl ribose

<400> SEQUENCE: 69
caccgtggca tgctgatcca cgatt                                             25

<210> SEQ ID NO 70

```
<211> LENGTH: 21
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 70
gcuccaccuc gcgcuuggag c                                              21

<210> SEQ ID NO 71
<211> LENGTH: 29
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 71
cugggauuag cuccaccucg cgcucccag                                      29

<210> SEQ ID NO 72
<211> LENGTH: 24
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 72
cugggauuag cuccaccucc ccag                                           24

<210> SEQ ID NO 73
<211> LENGTH: 26
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 73
ggagcuaauc ccauaaaacu agcucc                                         26

<210> SEQ ID NO 74
<211> LENGTH: 27
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 74
cggaguaguu uuaugggauu agcuccg                                        27

<210> SEQ ID NO 75
<211> LENGTH: 30
<212> TYPE: RNA
<213> ORGANISM: Artificial
<220> FEATURE:
```

```
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 75
cggaggaaua guuuuauggg auuagcuccg                                      30

<210> SEQ ID NO 76
<211> LENGTH: 33
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 76
cugagaauag uuuuauggga uuagcucccu cag                                  33

<210> SEQ ID NO 77
<211> LENGTH: 30
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 77
cgagaauagu uuuaugggau uagcuccucg                                      30

<210> SEQ ID NO 78
<211> LENGTH: 22
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 78
cuaguuuuau gggauuagcu ag                                              22

<210> SEQ ID NO 79
<211> LENGTH: 27
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 79
cgagaauagu uuuaugggau uagcucg                                         27

<210> SEQ ID NO 80
<211> LENGTH: 29
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose
```

```
<400> SEQUENCE: 80
cugagaauag uuuuauggga uuagcucag                              29

<210> SEQ ID NO 81
<211> LENGTH: 33
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 81
cgaacugaga auaguuuuau gggauuaggu ucg                         33

<210> SEQ ID NO 82
<211> LENGTH: 22
<212> TYPE: RNA
<213> ORGANISM: Artificial
<220> FEATURE:
<223> OTHER INFORMATION: Amplification and Detection Oligonucleotide
<220> FEATURE:
<221> NAME/KEY: misc_feature
<223> OTHER INFORMATION: 2'-O-methyl ribose

<400> SEQUENCE: 82
ccgaacugag aauaguguuc gg                                     22

<210> SEQ ID NO 83
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 83
aatttaatac gactcactat agggagacta cacacgtgct acaatggata ctacaaa    57

<210> SEQ ID NO 84
<211> LENGTH: 57
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (57)..(57)
<223> OTHER INFORMATION: Blocking Moiety

<400> SEQUENCE: 84
aatttaatac gactcactat agggagacta cacacgtgct acaatggcta gtacaaa    57

<210> SEQ ID NO 85
<211> LENGTH: 60
<212> TYPE: DNA
<213> ORGANISM: Artificial
<220> FEATURE:
```

```
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (60)..(60)
<223> OTHER INFORMATION: Blocking Moiety

<400> SEQUENCE: 85
aatttaatac gactcactat agggagacac gtgctacaat ggatactaca aagggtcgcg    60

<210> SEQ ID NO 86
<211> LENGTH: 60
<212> TYPE: DNA
<213> ORGANISM: Artificial
<220> FEATURE:
<223> OTHER INFORMATION: Amplification and Detection Oligonucleotide
<220> FEATURE:
<221> NAME/KEY: promoter
<222> LOCATION: (1)..(27)
<220> FEATURE:
<221> NAME/KEY: modified_base
<222> LOCATION: (60)..(60)
<223> OTHER INFORMATION: Blocking Moiety

<400> SEQUENCE: 86
aatttaatac gactcactat agggagacac gtgctacaat ggctagtaca aagggtcgcg    60

<210> SEQ ID NO 87
<211> LENGTH: 21
<212> TYPE: DNA
<213> ORGANISM: Artificial
<220> FEATURE:
<223> OTHER INFORMATION: Amplification and Detection Oligonucleotide

<400> SEQUENCE: 87
gagaatagtt ttatgggatt a                                              21

<210> SEQ ID NO 88
<211> LENGTH: 21
<212> TYPE: DNA
<213> ORGANISM: Artificial
<220> FEATURE:
<223> OTHER INFORMATION: Amplification and Detection Oligonucleotide

<400> SEQUENCE: 88
gagaatagtt ttatgggatc a                                              21

<210> SEQ ID NO 89
<211> LENGTH: 21
<212> TYPE: DNA
<213> ORGANISM: Artificial
<220> FEATURE:
<223> OTHER INFORMATION: Amplification and Detection Oligonucleotide

<400> SEQUENCE: 89
gagaatagtt ttatgcgatt a                                              21

<210> SEQ ID NO 90
<211> LENGTH: 21
<212> TYPE: DNA
<213> ORGANISM: Artificial
<220> FEATURE:
<223> OTHER INFORMATION: Amplification and Detection Oligonucleotide

<400> SEQUENCE: 90
gagaatactt ttatgggatt a                                              21
```

<210> SEQ ID NO 91
<211> LENGTH: 23
<212> TYPE: DNA
<213> ORGANISM: Artificial
<220> FEATURE:
<223> OTHER INFORMATION: Amplification and Detection Oligonucleotide

<400> SEQUENCE: 91
ctgagaatag ttttatggga tta                                              23

<210> SEQ ID NO 92
<211> LENGTH: 23
<212> TYPE: DNA
<213> ORGANISM: Artificial
<220> FEATURE:
<223> OTHER INFORMATION: Amplification and Detection Oligonucleotide

<400> SEQUENCE: 92
ctgagaatag ttttatggga tca                                              23

<210> SEQ ID NO 93
<211> LENGTH: 23
<212> TYPE: DNA
<213> ORGANISM: Artificial
<220> FEATURE:
<223> OTHER INFORMATION: Amplification and Detection Oligonucleotide

<400> SEQUENCE: 93
ctgagaatag ttttatgcga tta                                              23

<210> SEQ ID NO 94
<211> LENGTH: 23
<212> TYPE: DNA
<213> ORGANISM: Artificial
<220> FEATURE:
<223> OTHER INFORMATION: Amplification and Detection Oligonucleotide

<400> SEQUENCE: 94
ctgagaatac ttttatggga tta                                              23

<210> SEQ ID NO 95
<211> LENGTH: 28
<212> TYPE: DNA
<213> ORGANISM: Artificial
<220> FEATURE:
<223> OTHER INFORMATION: Amplification and Detection Oligonucleotide

<400> SEQUENCE: 95
ccgaactgag aatagtttta tgggatta                                         28

<210> SEQ ID NO 96
<211> LENGTH: 28
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(5)
<223> OTHER INFORMATION: 2'-O-methyl ribose

<400> SEQUENCE: 96
ccgaactgag aatagtttta tgggatta                                         28

```
<210> SEQ ID NO 97
<211> LENGTH: 28
<212> TYPE: DNA
<213> ORGANISM: Artificial
<220> FEATURE:
<223> OTHER INFORMATION: Amplification and Detection Oligonucleotide

<400> SEQUENCE: 97
ccgaactgag aatagttttta tgggatca                                28

<210> SEQ ID NO 98
<211> LENGTH: 28
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(5)
<223> OTHER INFORMATION: 2'-O-methyl ribose

<400> SEQUENCE: 98
ccgaactgag aatagttttta tgggatca                                28

<210> SEQ ID NO 99
<211> LENGTH: 28
<212> TYPE: DNA
<213> ORGANISM: Artificial
<220> FEATURE:
<223> OTHER INFORMATION: Amplification and Detection Oligonucleotide

<400> SEQUENCE: 99
ccgaactgag aatagttttta tgcgatta                                28

<210> SEQ ID NO 100
<211> LENGTH: 28
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
<222> LOCATION: (1)..(5)
<223> OTHER INFORMATION: 2'-O-methyl ribose

<400> SEQUENCE: 100
ccgaactgag aatagttttta tgcgatta                                28

<210> SEQ ID NO 101
<211> LENGTH: 28
<212> TYPE: DNA
<213> ORGANISM: Artificial
<220> FEATURE:
<223> OTHER INFORMATION: Amplification and Detection Oligonucleotide

<400> SEQUENCE: 101
ccgaactgag aatactttta tgggatta                                 28

<210> SEQ ID NO 102
<211> LENGTH: 28
<212> TYPE: DNA
<213> ORGANISM: Artificial
<220> FEATURE:
<223> OTHER INFORMATION: Amplification and Detection DNA-RNA Hybrid
      Oligonucleotide
<220> FEATURE:
<221> NAME/KEY: misc_feature
```

```
<222> LOCATION: (1)..(5)
<223> OTHER INFORMATION: 2'-O-methyl ribose

<400> SEQUENCE: 102
ccgaactgag aatactttta tgggatta                                          28

<210> SEQ ID NO 103
<211> LENGTH: 156
<212> TYPE: DNA
<213> ORGANISM: Artificial
<220> FEATURE:
<223> OTHER INFORMATION: E.coli

<400> SEQUENCE: 103
gcagcagtgg ggaatattgc acaatgggcg caagcctgat gcagccatgc cgcgtgtatg       60
aagaaggcct tcgggttgta aagtactttc agcggggagg aagggagtaa agttaatacc      120
tttgctcatt gacgttaccc gcagaagaag caccgg                                156

<210> SEQ ID NO 104
<211> LENGTH: 156
<212> TYPE: DNA
<213> ORGANISM: Artificial
<220> FEATURE:
<223> OTHER INFORMATION: L.monocytogenes

<400> SEQUENCE: 104
gcagcagtag ggaatcttcc gcaatggacg aaagtctgac ggagcaacgc cgcgtgtatg       60
aagaaggttt tcggatcgta aagtactgtt gttagagaag aacaaggata agagtaactg      120 cttgtcccctt gacggtatct aaccagaaag ccacgg                               156

<210> SEQ ID NO 105
<211> LENGTH: 156
<212> TYPE: DNA
<213> ORGANISM: Artificial
<220> FEATURE:
<223> OTHER INFORMATION: L.innocua

<400> SEQUENCE: 105
gcagcagtag ggaatcttcc gcaatggacg aaagtctgac ggagcaacgc cgcgtgtatg       60
aagaaggttt tcggatcgta aagtactgtt gttagagaag aacaaggata agagtaactg      120 cttgtcccctt gacggtatct aaccagaaag ccacgg                               156

<210> SEQ ID NO 106
<211> LENGTH: 156
<212> TYPE: DNA
<213> ORGANISM: Artificial
<220> FEATURE:
<223> OTHER INFORMATION: L.ivanovii

<400> SEQUENCE: 106
gcagcagtag ggaatcttcc gcaatggacg aaagtctgac ggagcaacgc cgcgtgtatg       60
aagaaggttt tcggatcgta aagtactgtt gttagagaag aacaaggata agagtaactg      120 cttgtcccctt gacggtatct aaccagaaag ccacgg                               156

<210> SEQ ID NO 107
<211> LENGTH: 156
<212> TYPE: DNA
<213> ORGANISM: Artificial
<220> FEATURE:
<223> OTHER INFORMATION: L.seeligeri
```

<400> SEQUENCE: 107

```
gcagcagtag ggaatcttcc gcaatggacg aaagtctgac ggagcaacgc cgcgtgtatg    60
aagaaggttt tcggatcgta aagtactgtt gttagagaag aacaaggata agagtaactg   120
cttgtcccctt gacggtatct aaccagaaag ccacgg                             156
```

<210> SEQ ID NO 108
<211> LENGTH: 156
<212> TYPE: DNA
<213> ORGANISM: Artificial
<220> FEATURE:
<223> OTHER INFORMATION: L.welshimeri

<400> SEQUENCE: 108

```
gcagcagtag ggaatcttcc gcaatggacg aaagtctgac ggagcaacgc cgcgtgtatg    60
aagaaggttt tcggatcgta aagtactgtt gttagagaag aacaaggata agagtaactg   120
cttgtcccctt gacggtatct aaccagaaag ccacgg                             156
```

<210> SEQ ID NO 109
<211> LENGTH: 156
<212> TYPE: DNA
<213> ORGANISM: Artificial
<220> FEATURE:
<223> OTHER INFORMATION: L.murrayi

<400> SEQUENCE: 109

```
gcagcagtag ggaatcttcc gcaatggacg aaagtctgac ggagcaacgc cgcgtgtgtg    60
aagaaggttt tcggatcgta aagcactgtt gttagagaag aacaaggata agagtaactg   120
cttgtcccctt gacggtatct aaccagaaag ccacgg                             156
```

<210> SEQ ID NO 110
<211> LENGTH: 156
<212> TYPE: DNA
<213> ORGANISM: Artificial
<220> FEATURE:
<223> OTHER INFORMATION: L.grayi

<400> SEQUENCE: 110

```
gcagcaatag ggaaacttcc gcaatggacg aaagtctgac ggagcaacgc cgcgtgtgtg    60
aagaaggttt tcggatcgta aagcactgtt gttagagaag aacaaggata agagtaactg   120
cttgtcccctt gacggtatct aaccagaaag ccacgg                             156
```

<210> SEQ ID NO 111
<211> LENGTH: 156
<212> TYPE: DNA
<213> ORGANISM: Artificial
<220> FEATURE:
<223> OTHER INFORMATION: B.thermosphacta

<400> SEQUENCE: 111

```
gcagcagtag ggaatcttcg gcaatggacg aaagtctgac cgagcaacgc cgcgtgagcg    60
aagaaggcct tcgggtcgta aagctctgtt gttagagaag aacatgggtg agagtaactg   120
ttcaccccctt gacggtatct aaccagaaag ccacgg                             156
```

<210> SEQ ID NO 112
<211> LENGTH: 156
<212> TYPE: DNA
<213> ORGANISM: Artificial
<220> FEATURE:
<223> OTHER INFORMATION: E.rhusiopathiae -continued

<400> SEQUENCE: 112

```
gcagcagtag ggaattttcg gcaatggggg aaaccctgac cgagcaacgc cgcgtgagtg      60
aagacggcct tcgggttgta aagctctgtt gtaagggaag aacgatagga agagggaatg     120
cttcttatat gacggtacct taccagaaag ccacgg                               156
```

<210> SEQ ID NO 113
<211> LENGTH: 191
<212> TYPE: DNA
<213> ORGANISM: Artificial
<220> FEATURE:
<223> OTHER INFORMATION: E.coli

<400> SEQUENCE: 113

```
ggtggggatg acgtcaagtc atcatggccc ttacgaccag ggctacacac gtgctacaat      60
ggcgcataca aagagaagcg acctcgcgag agcaagcgga cctcataaag tgcgtcgtag     120
tccggattgg agtctgcaac tcgactccat gaagtcggaa tcgctagtaa tcgtggatca     180
gaatgccacg g                                                          191
```

<210> SEQ ID NO 114
<211> LENGTH: 191
<212> TYPE: DNA
<213> ORGANISM: Artificial
<220> FEATURE:
<223> OTHER INFORMATION: L.monocytogenes
<220> FEATURE:
<221> NAME/KEY: misc_feature
<222> LOCATION: (77)..(77)
<223> OTHER INFORMATION: a or g or c or t/u, unknown, or other

<400> SEQUENCE: 114

```
ggtggggatg acgtcaaatc atcatgcccc ttatgacctg gctacacac gtgctacaat       60
ggatagtaca aagggtngcg aagccgcgag gtggagctaa tcccataaaa ctattctcag     120
ttcggattgt aggctgcaac tcgcctacat gaagccggaa tcgctagtaa tcgtggatca     180
gcatgccacg g                                                          191
```

<210> SEQ ID NO 115
<211> LENGTH: 191
<212> TYPE: DNA
<213> ORGANISM: Artificial
<220> FEATURE:
<223> OTHER INFORMATION: L.innocua

<400> SEQUENCE: 115

```
ggtggggatg acgtcaaatc atcatgcccc ttatgacctg gctacacac gtgctacaat       60
ggatggtaca aagggtcgcg aagccgcgag gtggagccaa tcccataaaa ccattctcag     120
ttcggattgt aggctgcaac tcgcctacat gaagccggaa tcgctagtaa tcgtggatca     180
gcatgccacg g                                                          191
```

<210> SEQ ID NO 116
<211> LENGTH: 191
<212> TYPE: DNA
<213> ORGANISM: Artificial
<220> FEATURE:
<223> OTHER INFORMATION: L.ivanovii

<400> SEQUENCE: 116

```
ggtggggatg acgtcaaatc atcatgcccc ttatgacctg gctacacac gtgctacaat       60
```
ggatggtaca aagggtcgcg aagccgcgag gtggagccaa tcccataaaa ccattctcag   120
ttcggattgt aggctgcaac tcgcctacat gaagccggaa tcgctagtaa tcgcggatca   180
gcatgccgcg g   191

<210> SEQ ID NO 117
<211> LENGTH: 191
<212> TYPE: DNA
<213> ORGANISM: Artificial
<220> FEATURE:
<223> OTHER INFORMATION: L.seeligeri

<400> SEQUENCE: 117
ggtggggatg acgtcaaatc atcatgcccc ttatgacctg gctacacac gtgctacaat   60 ggatggtaca aagggtagcg aagccgcgag gtggagccaa tcccataaaa ccattctcag   120
ttcggattgt aggctgcaac tcgcctacat gaagccggaa tcgctagtaa tcgtggatca   180
gcatgccacg g   191

<210> SEQ ID NO 118
<211> LENGTH: 191
<212> TYPE: DNA
<213> ORGANISM: Artificial
<220> FEATURE:
<223> OTHER INFORMATION: L.welshimeri

<400> SEQUENCE: 118
ggtggggatg acgtcaaatc atcatgcccc ttatgacctg gctacacac gtgctacaat   60 ggatggtaca aagggtcgcg aagccgcgag gtggagccaa tcccataaaa ccattctcag   120
ttcggattgt aggctgcaac tcgcctacat gaagccggaa tcgctagtaa tcgtggatca   180
gcatgccacg g   191

<210> SEQ ID NO 119
<211> LENGTH: 191
<212> TYPE: DNA
<213> ORGANISM: Artificial
<220> FEATURE:
<223> OTHER INFORMATION: L.murrayi

<400> SEQUENCE: 119
ggtggggatg acgtcaaatc atcatgcccc ttatgacctg gctacacac gtgctacaat   60 ggatgataca aagggtcgcg aagccgcgag gtgaagctaa tcccataaaa tcattctcag   120
ttcggattgt aggctgcaac tcgcctacat gaagccggaa tcgctagtaa tcgcggatca   180
gcatgccgcg g   191

<210> SEQ ID NO 120
<211> LENGTH: 190
<212> TYPE: DNA
<213> ORGANISM: Artificial
<220> FEATURE:
<223> OTHER INFORMATION: L.grayi

<400> SEQUENCE: 120
ggtggggatg acgtcaaatc atcatgcccc ttatgacctg gctacacac gtgctacaat   60 ggatgataca aagggtcgcg aaccgcgagg tgaagctaat cccataaaat cattctcagt   120
tcggattgta ggctgcaact cgcctacatg aagccggaat cgctagtaat cgcggatcag   180
catgccgcgg   190

```
<210> SEQ ID NO 121
<211> LENGTH: 134
<212> TYPE: DNA
<213> ORGANISM: Artificial
<220> FEATURE:
<223> OTHER INFORMATION: B.thermosphacta

<400> SEQUENCE: 121
aatggataat acaaagggtc gcgaagccgc gaggtggagc caatcccata aaattattct      60
cagttcggat tgcaggctgc aactcgcctg catgaagccg gaatcgctag taatcgtaga     120
tcagcatgct acgg                                                      134

<210> SEQ ID NO 122
<211> LENGTH: 191
<212> TYPE: DNA
<213> ORGANISM: Artificial
<220> FEATURE:
<223> OTHER INFORMATION: E.rhusiopathiae

<400> SEQUENCE: 122
ggtggggatg acgtcaaatc atcatgcccc ttatgatctg ggctacacac gtactacaat      60
ggcgtataca gagggcagcg aagcagcgat gcggagcgaa tctcagaaag tacgtctcag     120
ttcggattgg agtctgcaac tcgactccat gaagtcggaa tcgctagtaa tcgcggatca     180
gaatgccgcg g                                                         191
```